(12) United States Patent
Kurono

(10) Patent No.: US 7,231,834 B2
(45) Date of Patent: Jun. 19, 2007

(54) STRIDE MEASURING APPARATUS

(75) Inventor: Takehiro Kurono, Hamamatsu (JP)

(73) Assignee: Hamamatsu Photonics K. K., Shizuoka (JP)

( * ) Notice: Subject to any disclaimer, the term of this patent is extended or adjusted under 35 U.S.C. 154(b) by 55 days.

(21) Appl. No.: 10/899,138

(22) Filed: Jul. 27, 2004

(65) Prior Publication Data

US 2005/0039541 A1 Feb. 24, 2005

(30) Foreign Application Priority Data

Jul. 28, 2003 (JP) ............................ P2003-281297

(51) Int. Cl.
*G01L 1/24* (2006.01)
*A61B 5/103* (2006.01)

(52) U.S. Cl. ............................ 73/800; 348/61; 600/595

(58) Field of Classification Search ................. 73/800; 348/61

See application file for complete search history.

(56) References Cited

U.S. PATENT DOCUMENTS

| | | | | |
|---|---|---|---|---|
| 4,600,016 A | | 7/1986 | Boyd et al. ................. | 128/782 |
| 4,774,679 A | | 9/1988 | Carlin ........................ | 364/550 |
| 5,120,228 A | * | 6/1992 | Stahl et al. ................. | 434/258 |
| 5,299,454 A | | 4/1994 | Fuglewicz et al. ........... | 73/172 |
| 5,312,310 A | * | 5/1994 | Shimizu et al. .............. | 482/54 |
| 5,483,630 A | | 1/1996 | Unuma et al. .............. | 395/152 |
| 5,524,637 A | | 6/1996 | Erickson ..................... | 128/779 |
| 5,577,981 A | | 11/1996 | Jarvik ........................... | 482/4 |
| 5,831,937 A | | 11/1998 | Weir et al. ................... | 367/128 |
| 6,010,465 A | | 1/2000 | Nashner ..................... | 600/595 |
| 6,205,245 B1 | | 3/2001 | Yuan et al. ................. | 382/162 |
| 6,231,527 B1 | * | 5/2001 | Sol ............................ | 600/595 |
| 6,256,461 B1 | | 7/2001 | Takeyama et al. .......... | 399/66 |
| 6,590,536 B1 | | 7/2003 | Walton ....................... | 342/463 |
| 6,645,126 B1 | | 11/2003 | Martin et al. ................ | 482/54 |
| 6,899,686 B2 | * | 5/2005 | Hampton et al. ........... | 600/595 |
| 2003/0055362 A1 | * | 3/2003 | Hampton .................... | 600/595 |

FOREIGN PATENT DOCUMENTS

| | | |
|---|---|---|
| JP | 2-47231 | 10/1990 |
| JP | 7-45239 | 10/1995 |
| JP | 10-43327 | 2/1998 |
| JP | 2001-170029 | 6/2001 |
| JP | 2001-324306 | 11/2001 |
| JP | 2002-277213 | 9/2002 |
| JP | 2004-028635 | 1/2004 |
| JP | 2004-167002 | 6/2004 |

* cited by examiner

*Primary Examiner*—Edward Lefkowitz
*Assistant Examiner*—Freddie Kirkland, III
(74) *Attorney, Agent, or Firm*—Drinker Biddle & Reath LLP

(57) ABSTRACT

In a stride measuring apparatus, a signal wave emitter and a signal wave detector are opposed to each other in a direction intersecting with a predetermined direction in which the running surface is driven. The signal wave emitter emits a light beam. The signal wave detector outputs an ON signal when receiving the light beam, and outputs an OFF signal when the light beam is intercepted. A detector part calculates a moving speed on the basis of a difference between a fall time and a rise time of one OFF signal out of two OFF signals outputted in succession from the signal wave detector, and a foot size of a subject. The detector part calculates a difference between output times of the two OFF signals (stride time) and calculates a stride on the basis of a product of the moving speed and the stride time.

14 Claims, 16 Drawing Sheets

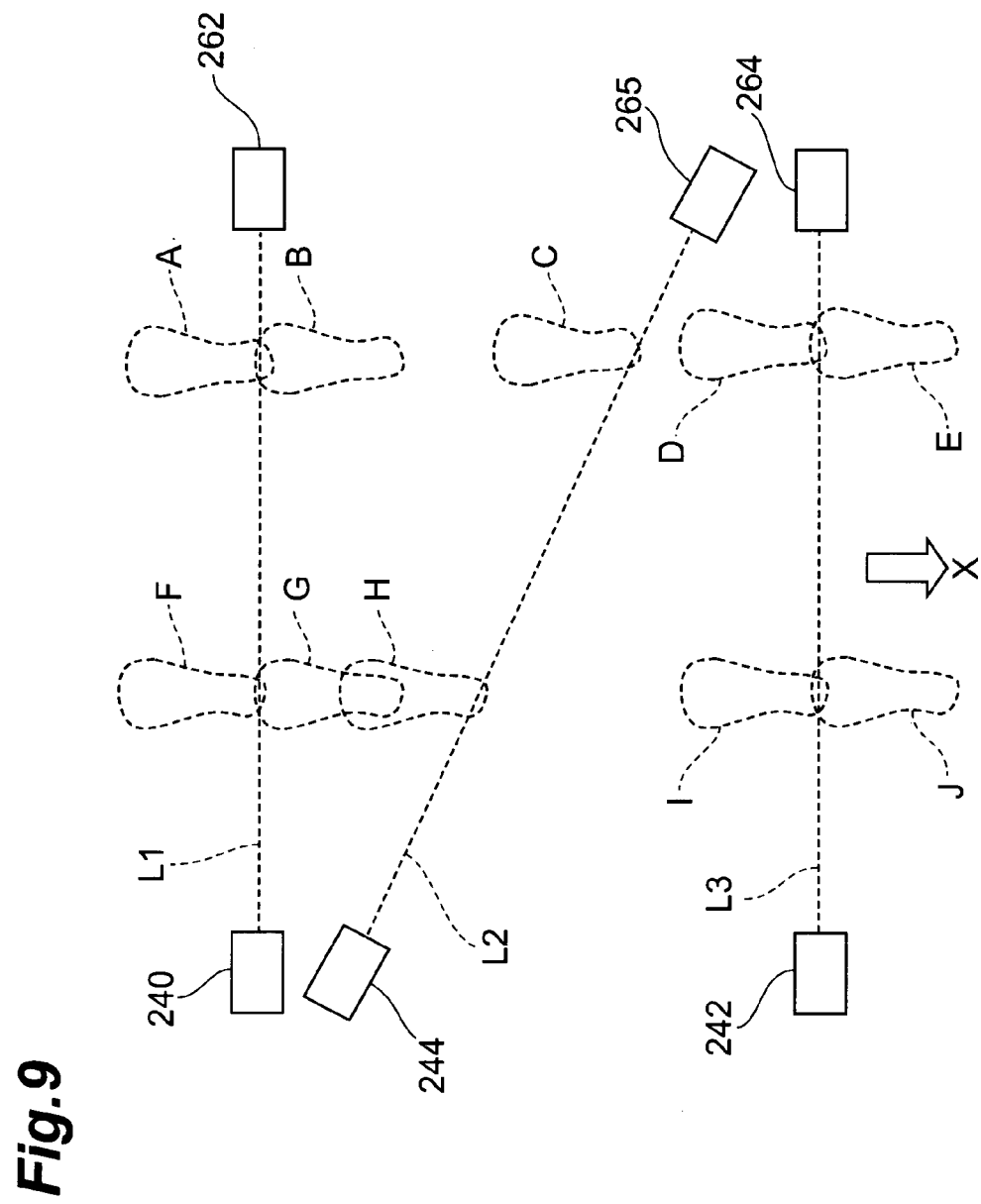

STRIDE MEASURING APPARATUS

BACKGROUND OF THE INVENTION

1. Field of the Invention

The present invention relates to stride measuring apparatus capable of measuring a stride of a subject running or walking on a running surface of a belt.

2. Related Background of the Invention

A running machine with a belt driven at predetermined speed, so called a treadmill, is in widespread use at sports clubs and others. It is important in view of checking a running posture, to accurately measure a stride of a subject running or walking (hereinafter, both being referred to as running) on a running surface of a belt of a treadmill. As a conventional stride measuring apparatus for measuring a stride of a subject running on the running surface, there is an apparatus provided with a video camera as a sensor and configured to calculate the stride of the subject on the basis of images of feet of the running subject taken by the video camera (e.g., reference is made to Japanese Patent Application Laid-Open No. JP-A-2002-277213).

SUMMARY OF THE INVENTION

The conventional stride measuring apparatus described above permitted the measurement of stride with high, accuracy but required a space for installation of the video camera, and there are desires for stride measuring apparatus that can be installed even in a narrower space.

An object of the present invention is to provide stride measuring apparatus constructed in a compact scale enough to be installed in a narrow space.

In order to achieve the above object, a stride measuring apparatus according to the present invention comprises a belt, signal wave emitting means, signal wave detecting means, moving speed calculating means, stride time calculating means, and stride calculating means. The belt has a running surface for a subject to run or walk, and is driven in a predetermined direction. The signal wave emitting means is placed at a position along an edge part of the running surface and is configured to emit a signal wave in a direction intersecting with the predetermined direction and at a predetermined height above the running surface. The signal wave detecting means is placed at an edge part of the running surface and is configured to receive the signal wave emitted by the signal wave emitting means and to output a first signal when a foot of the subject passes across the signal wave and a second signal when no foot of the subject passes across the signal wave. The moving speed calculating means calculates a moving time based on a calculation of a difference between a rise time and a fall time of one of two first signals outputted in succession from the signal wave detecting means, and calculates a moving speed of the subject on the basis of a calculation of a quotient between a size of the feet of the subject and the moving time. The stride time calculating means calculates a stride time based on a calculation of a difference between output times of the two first signals. The stride calculating means calculates a stride of the subject, based on a calculation of a product between the stride time calculated by the stride time calculating means and the moving speed calculated by the moving speed calculating means.

The above configuration comprises the signal wave emitting means and the signal wave detecting means placed at their respective positions along the edge part of the running surface, as a sensor, so as to permit the calculation of the stride, thus providing the compact stride measuring apparatus.

Preferably, the stride measuring apparatus according to the present invention further comprises second signal wave emitting means placed at a position along an edge part of the running surface and configured to emit a second signal wave in a direction intersecting with the predetermined direction and at a predetermined height above the running surface so as to be inclined at a predetermined angle relative to the emission direction of the aforementioned signal wave; second signal wave detecting means placed at a position along an edge part of the running surface and configured to receive the second signal wave emitted by the second signal wave emitting means and to output a first signal when a foot of the subject passes across the second signal wave and a second signal where no foot of the subject passes across the second signal wave; and left/right determining means for determining whether the stride calculated by the stride calculating means is a stride of the left foot or a stride of the right foot, based on a comparison of a time difference between first signals respectively outputted from the signal wave detecting means and from the second signal wave detecting means, with a time difference between first signals respectively outputted in succession from the signal wave detecting means and from the second signal wave detecting means.

Since in the above configuration the second signal wave is emitted in the emission direction as inclined relative to the emission direction of the signal wave, a time of the left foot from an intersection with the signal wave to an intersection with the second signal wave is different from that of the right foot. Therefore, whether the stride calculated by the stride calculating means is a stride of the left foot or a stride of the right foot of the subject can be determined by the comparison of the time difference between the output times of the first signals respectively outputted from the signal wave detecting means and from the second signal wave detecting means, with the time difference between the output times of the first signals respectively outputted in succession from the signal wave detecting means and from the second signal wave detecting means.

The stride measuring apparatus according to the present invention may also be configured so that the signal wave emitting means is placed at a position along one edge part of the running surface and so that the signal wave detecting means is placed at a position along another edge part of the running surface and opposite the signal wave emitting means and is configured to output a first signal when the signal wave from the signal wave emitting means is intercepted and to output a second signal when the signal wave from the signal wave emitting means is detected.

The stride measuring apparatus according to the present invention may also be configured so that the signal wave emitting means is placed at a position along one edge part of the running surface and so that the signal wave detecting means is placed at a position along the one edge part of the running surface so as to detect the signal wave emitted from the signal wave emitting means and reflected from a foot of the subject and is configured to output a first signal when the signal wave is detected and to output a second signal when the signal wave is not detected.

In order to achieve the above object, another stride measuring apparatus according to the present invention comprises a belt, first signal wave emitting means, second signal wave emitting means, first signal wave detecting means, second signal wave detecting means, moving speed calculating means, stride time calculating means, and stride calculating means. The belt has a running surface for a subject to run or walk and is driven in a predetermined direction. The first signal wave emitting means is placed at a position along an edge part of the running surface and is configured to emit a first signal wave in a direction intersecting with the predetermined direction and at a height above the running surface. The second signal wave emitting means is placed a predetermined distance apart from the first signal wave emitting means in the predetermined direction and is configured to output a second signal wave in a direction intersecting with the predetermined direction and at a predetermined height above the running surface. The first signal wave detecting means is placed at an edge part of the running surface and is configured to receive the first signal wave emitted by the first signal wave emitting means and to output a first signal when a foot of the subject passes across the first signal wave and a second signal when no foot of the subject passes across the first signal wave. The second signal wave detecting means is placed at an edge part of the running surface and is configured to receive the second signal wave emitted by the second signal wave emitting means and to output a first signal when a foot of the subject passes across the second signal wave and a second signal when no foot of the subject passes across the second signal wave. The moving speed calculating means calculates a moving time based on a calculation of a difference between an output time of a first signal outputted from the first signal wave detecting means and an output time of a first signal outputted subsequently thereto from the second signal wave detecting means, and calculates a moving speed of the subject on the basis of a calculation of a quotient between a predetermined distance and the moving time. The stride time calculating means calculates a stride time based on a calculation of a difference between output times of two first signals outputted in succession from one of the first and second signal wave detecting means. The stride calculating means calculates a stride of the subject, based on a calculation of a product between the stride time calculated by the stride time calculating means and the moving speed calculated by the moving speed calculating means.

The above configuration comprises the first and second signal wave emitting means and the first and second signal wave detecting means placed at the edge part of the running surface, as a sensor, so as to permit the calculation of the stride, thus providing the compact stride measuring apparatus.

Preferably, the stride measuring apparatus according to the present invention further comprises third signal wave emitting means placed at a position along an edge part of the running surface and configured to emit a third signal wave in a direction intersecting with the predetermined direction and at a predetermined height above the running surface so as to be inclined at a predetermined angle relative to the emission direction of the first and second signal waves; third signal wave detecting means placed at an edge part of the running surface and configured to receive the third signal wave emitted by the third signal wave emitting means and to output a first signal when a foot of the subject passes across the third signal wave and a second signal when no foot of the subject passes across the third signal wave; and left/right determining means for determining whether the stride calculated by the stride calculating means is a stride of the left foot or a stride of the right foot of the subject, based on a comparison of a time difference between output times of first signals respectively outputted from one of the first and second signal wave detecting means and from the third signal wave detecting means, with a time difference between output times of first signals respectively outputted in succession from said one signal wave detecting means and from the third signal wave detecting means.

Since in the above configuration the third signal wave is emitted in the emission direction as inclined relative to the emission direction of the first and second signal waves, a time of the left foot from an intersection with one of the first and second signal waves to an intersection with the third signal wave is different from that of the right foot. Therefore, whether the stride calculated by the stride calculating means is a stride of the left foot or a stride of the right foot of the subject can be determined by the comparison of the time difference between output times of first signals respectively outputted from one of the first and second signal wave detecting means detecting the aforementioned one signal wave and from the third signal wave detecting means, with the time difference between output times of first signals respectively outputted in succession from the aforementioned one signal wave detecting means and from the third signal wave detecting means.

The stride measuring apparatus according to the present invention can be configured so that the first and second signal wave emitting means are placed at positions along one edge part of the running surface and so that the first signal wave detecting means and the second signal wave detecting means are arranged as follows. The first signal wave detecting means is placed at a position along another edge part of the belt and opposite the first signal wave emitting means and is configured to output a first signal when the first signal wave from the first signal wave emitting means is intercepted and to output a second signal when the signal wave from the first signal wave emitting means is detected. The second signal wave detecting means is placed at a position along another edge part of the belt and opposite the second signal wave emitting means and is configured to output a first signal when the second signal wave from the second signal wave emitting means is intercepted and to output a second signal when the signal wave from the second signal wave emitting means is detected.

The stride measuring apparatus according to the present invention may be configured so that the first and second signal wave emitting means are placed at positions along one edge part of the running surface, the first signal wave detecting means is placed at a position along another edge part of the running surface and opposite the first signal wave emitting means and is configured to output a first signal when the first signal wave from the first signal wave emitting means is intercepted and to output a second signal when the signal wave from the first signal wave emitting means is detected, and the second signal wave detecting means is placed at a position along another edge part of the running surface and opposite the second signal wave emitting means and is configured to output a first signal when the second signal wave from the second signal wave emitting means is intercepted and to output a second signal when the signal wave from the second signal wave emitting means is detected.

The stride measuring apparatus according to the present invention may also be configured so that the first and second signal wave emitting means are placed at positions along one edge part of the running surface, the first signal wave detecting means is placed at a position along one edge part of the running surface so as to detect the first signal wave emitted from the first signal wave emitting means and reflected from a foot of the subject, and is configured to output a first signal when the first signal wave is detected and to output a second signal when the first signal wave is not detected, and the second signal wave detecting means is placed at a position along one edge part of the running surface so as to detect the second signal wave emitted from the second signal wave emitting means and reflected from a foot of the subject and is configured to output a first signal when the second signal wave is detected and to output a second signal when the second signal wave is not detected.

In the stride measuring apparatus of the present invention, preferably, the moving speed calculating means calculates as the moving speed an average of a first moving speed calculated based on rise times of a first signal outputted from the first signal wave detecting means and a first signal outputted subsequently thereto from the second signal wave detecting means, and a second moving speed calculated based on fall times of the respective first signals.

Since in the above configuration the moving speed is the average of the first moving speed calculated from the rise times of the first signals and the second moving speed calculated from the fall times of the first signals, the moving speed can be calculated with accuracy.

Preferably, the stride measuring apparatus according to the present invention further comprises moving time removing means for removing the moving time when the moving time calculated by the moving speed calculating means is determined to be short based on a comparison according to a predetermined rule with a moving time calculated at a different time.

The moving time removing means removes the moving time when it is determined that the moving time calculated by the moving speed calculating means is short, based on the comparison according to the predetermined rule with the moving time calculated at the different time. Therefore, the stride measuring apparatus of the above configuration is able to remove the moving time generated from a shuffle or the like of the subject.

Another stride measuring apparatus of the present invention comprises a belt, a plurality of signal wave emitting means, a plurality of signal wave detecting means, line detecting means, and stride calculating means. The belt has a running surface for a subject to run or walk and is driven in a predetermined direction. The plurality of signal wave emitting means are placed at positions along an edge part of the running surface and at predetermined intervals and are configured to emit a signal wave in a direction intersecting with the predetermined direction and at a predetermined height above the running surface. The plurality of signal wave detecting means are placed at positions along an edge part of the running surface and are configured to receive a signal wave emitted from corresponding signal wave emitting means and to output a first signal when a foot of the subject passes across the signal wave and a second signal when no foot of the subject passes across the signal wave. The line detecting means detects a line that fits a variable set obtained when a foot of the subject moves in the predetermined direction. Variables in the variable set involve as parameters an output time of the first signal or the second signal outputted from the signal wave detecting means, and the position of the signal wave detecting means. The stride calculating means calculates the stride, based on a distance between intersecting points of a line passing an arbitrary time with two lines detected in succession by the line detecting means.

The above configuration comprises the signal wave emitting means and the signal wave detecting means placed at the positions along the edge part of the running surface, as a sensor, so as to permit the calculation of the stride, thus providing the compact stride measuring apparatus.

In the stride measuring apparatus of the present invention, the running surface of the belt is driven in the predetermined direction from one end to the other end. This stride measuring apparatus can further comprise landing time detecting means. The landing time detecting means detects from the variables in the variable set, a variable containing a position closest to the aforementioned one end as a parameter, the variable having an error within a predetermined value relative to the line detected with use of the variable set. The landing time detecting means detects a variable containing as parameters an output time later than the output time contained in the detected variable, and a position on the one end side relative to the position contained in the detected variable, and detects the output time contained in the detected variable, as a landing time. The stride calculating means can use the landing time as the aforementioned arbitrary time.

The stride measuring apparatus of the present invention can further comprise moving speed detecting means. The moving speed detecting means determines as a stride time a duration between two landing times detected in succession by the landing time detecting means, and calculates a foot speed, based on a calculation of a quotient between the stride time and the stride. The above configuration is able to calculate the foot speed of the subject, without using a sensor to measure the speed of the belt.

The stride measuring apparatus of the present invention can further comprise second signal wave emitting means, second signal wave detecting means, and left/right determining means. The second signal wave emitting means is placed at a position along an edge part of the running surface and is configured to emit a second signal wave in a direction intersecting with the predetermined direction. The second signal wave detecting means receives a reflected wave of the second signal wave. The left/right determining means determines whether the stride calculated by the stride calculating means is a stride of the left foot or a stride of the right foot of the subject, based on a period of time between an emission time and a reception time of the second signal wave. This configuration enables the apparatus to determine whether the stride is one of the left or right foot.

BRIEF DESCRIPTION OF THE DRAWINGS

FIG. 9 is an illustration showing states in which feet of a subject S running on a running surface pass across light beams L1, L3, and L2 with the passage of time;

DESCRIPTION OF THE PREFERRED EMBODIMENTS

Figure 1:
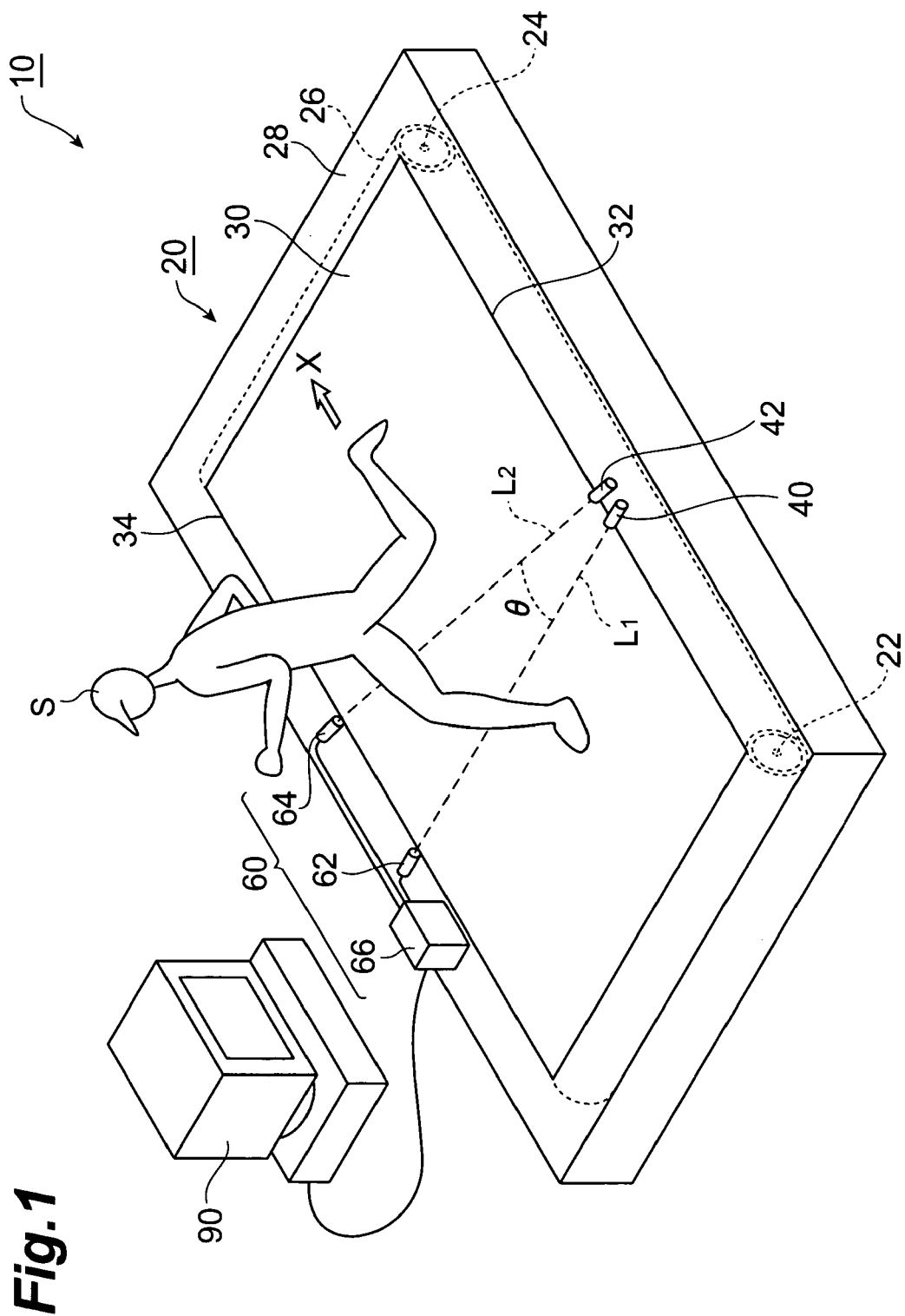
FIG. 1 is a perspective view schematically showing a stride measuring apparatus according to the first embodiment of the present invention.

The preferred embodiments of the stride measuring apparatus according to the present invention will be described below in detail with reference to the drawings. In the drawings the same or equivalent portions will be denoted by the same reference symbols.

A stride measuring apparatus 10 according to the first embodiment of the present invention will be described. FIG. 1 is a perspective view schematically showing the stride measuring apparatus according to the first embodiment of the present invention. The stride measuring apparatus 10 shown in FIG. 1 is a device for measuring a stride of a subject S running on a running surface 30 of a treadmill 20. The stride measuring apparatus 10 has a treadmill 20, a signal wave emitter 40 (signal wave emitting means), a second signal wave emitter 42 (second signal wave emitting means), a detector part 60, and a computer 90.

Inside the treadmill 20, a pair of rollers 22, 24 are set in parallel to, each other. An endless belt 26 is stretched between the rollers 22, 24 and a surface of the endless belt 26 exposed in a rectangular aperture of a cover 28 serves as a running surface 30. A driving unit (not shown) controls the rotating speed of the rollers 22, 24, whereby the running surface 30 of the endless belt 26 is driven in a predetermined direction (a direction indicated by arrow X in the figure).

The signal wave emitter 40 is placed at a position along one edge part 32 of the treadmill 20 and emits a signal wave L1 in a direction intersecting with the predetermined direction and at a predetermined height relative to the running surface 30. In the present embodiment, the signal wave emitter 40 is a light source to emit a light beam L1 as the signal wave L1 and is placed on the cover 28 extending along the edge part 32. The emission direction of the light beam L1 is a direction substantially perpendicular to the predetermined direction. The predetermined height at which the signal wave emitter 40 emits the light beam L1 is a height at which the light beam L1 is emitted in the range from the tiptoe to the heel of the side part of a foot (or shoe) of the subject S landing on the running surface 30. This predetermined height is, for example, a height of two or three centimeters from the running surface 30.

The second signal wave emitter 42 is placed at a position along one edge part 32 of the treadmill 20 and emits a second signal wave L2. In the present embodiment, the second signal wave emitter 42 is a light source to emit a light beam L2 as the second signal wave L2 and is placed on the cover 28 extending along the edge part 32. The second signal wave emitter 42 emits the light beam L2 at the predetermined height in the same manner as the signal wave emitter 40. The second signal wave emitter 42 emits the light beam L2 so as to be inclined at a predetermined angle relative to the emission direction of the light beam L1. This predetermined angle will be described later.

The detector part 60 has a signal wave detector 62 (signal wave detecting means), a second signal wave detector 64 (second signal wave detecting means), and a calculation part 66.

The signal wave detector 62 is placed at a position along another edge part 34 of the treadmill 20 and opposite the signal wave emitter 40, and detects the signal wave L1 emitted by the signal wave emitter 40. In the present embodiment, the signal wave detector 62 is equipped with a light receiving device for receiving the light beam L1, and is placed on the cover 28 extending along the edge part 34. The signal wave detector 62 outputs a first signal when the light beam L1 is intercepted, and outputs a second signal when the light beam L1 is detected, each to the calculation part 66.

In the present embodiment, where no foot of the subject S passes across the light beam L1 and where the light beam L1 is received, the signal wave detector 62 outputs an ON signal as a second signal to the calculation part 66. On the other hand, where a foot of the subject S passes across the light beam L1 and where the light beam L1 is thus intercepted, the signal wave detector 62 outputs an OFF signal as a first signal to the calculation part 66.

The second signal wave detector 64 is placed at a position along the other edge part 34 of the treadmill 20 so as to detect the second signal wave L2. In the present embodiment, the second signal wave detector 64 is equipped with a light receiving device for receiving the light beam L2, and is placed on the cover 28 extending along the edge part 34. The second signal wave detector 64 outputs to the calculation part 66 an OFF signal as a first signal when the light beam L2 from the second signal wave emitter 42 is intercepted, and outputs an ON signal as a second signal when the light beam L2 is received.

Figure 2:
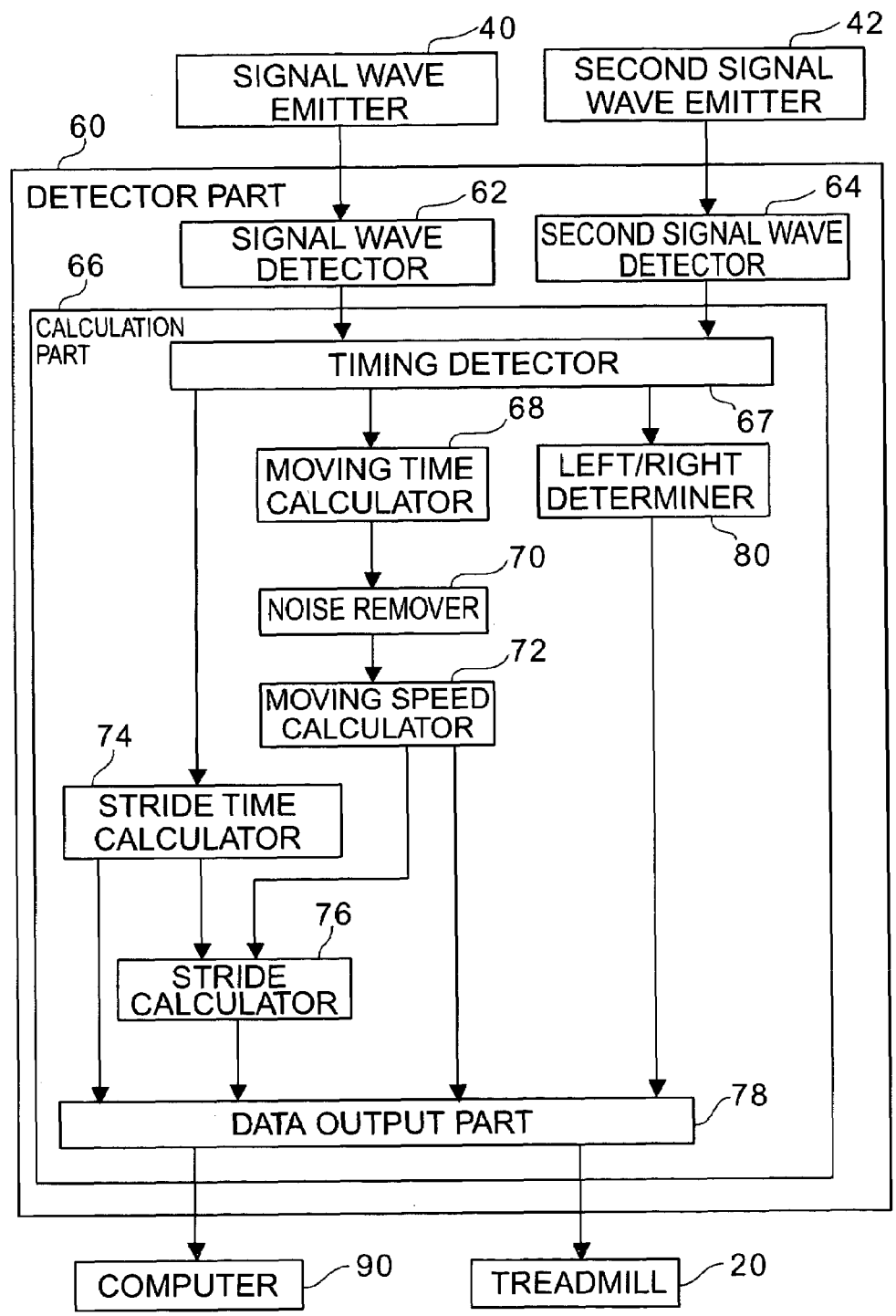
FIG. 2 is an illustration showing a configuration of a detector part in the stride measuring apparatus according to the first embodiment of the present invention.

The calculation part 66 will be described below in detail. FIG. 2 is an illustration showing a configuration of the detector part in the stride measuring apparatus according to the first embodiment of the present invention. The calculation part 66 shown in FIG. 2 has a timing detector 67, a moving time calculator 68, a noise remover 70, a moving speed calculator 72 (moving speed calculating means), a stride time calculator 74 (stride time calculating means), a stride calculator 76 (stride calculating means), a data output part 78, and a left/right determiner 80 (left/right determining means).

Figure 3:
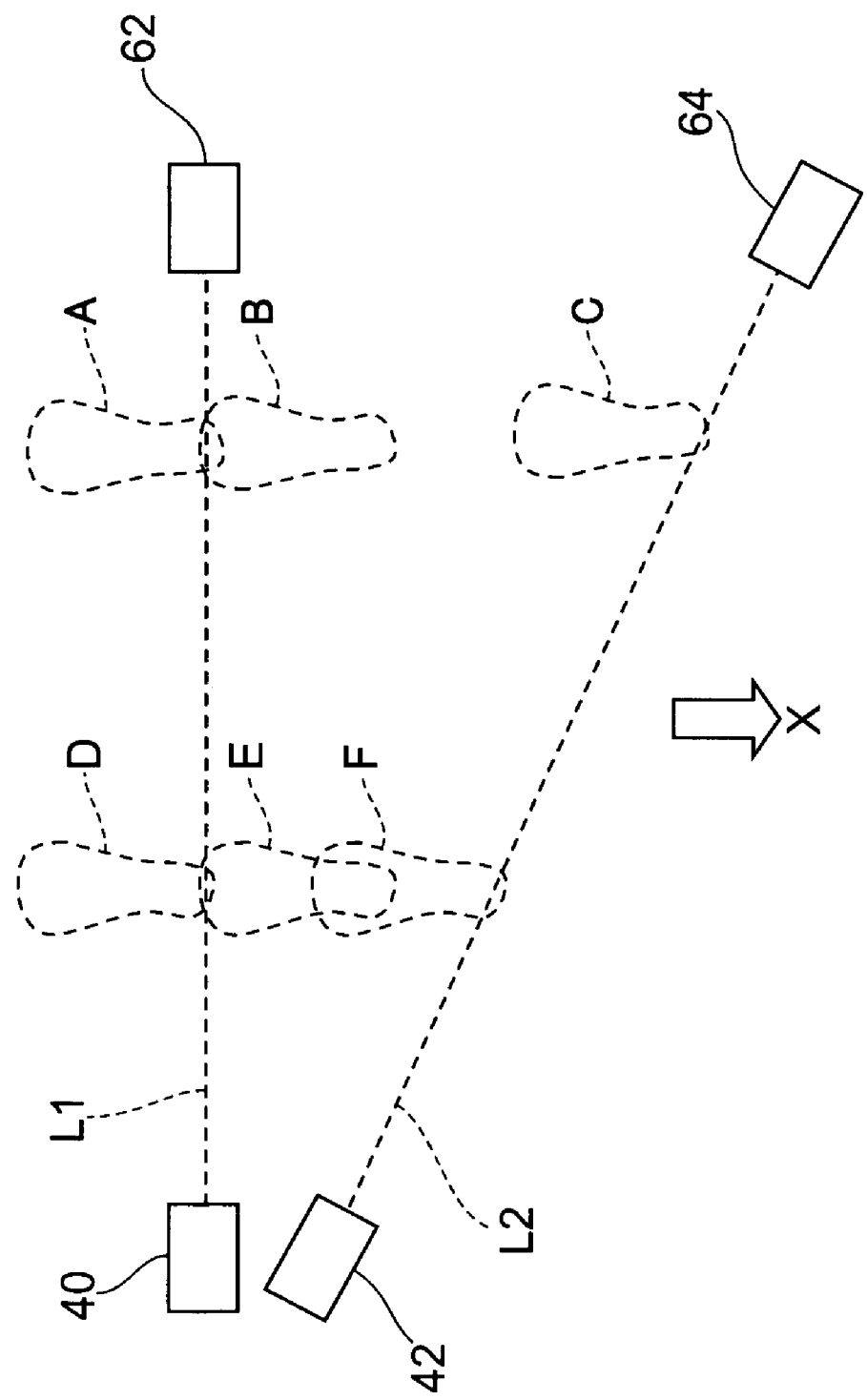
FIG. 3 is an illustration showing states in which feet of a subject S running on a running surface pass across light beams L1 and L2 with the passage of time.

The components of the calculation part 66 will be described below in detail with reference to FIG. 3 showing states in which the feet of the subject S running on the running surface pass across the light beams L1 and L2 with the passage of time, FIG. 4A being a timing chart of signals outputted from the signal wave detector 62 through the states A to F shown in FIG. 3, and FIG. 4B being a timing chart of signals outputted from the second signal wave detector 64 similarly. In the description hereinafter, subscripts n−1 and n will be used to indicate a sequence of time.

The timing detector 67 extracts a fall time $Ts1_n$ and a rise time $Te1_n$ of an OFF signal outputted from the signal wave detector 62, and outputs them to the moving speed calculator 72 and to the stride time calculator 74. The timing detector 67 also extracts a fall time $Ts2_n$ of an OFF signal outputted from the second signal wave detector 64, and outputs the fall time $Ts1_n$ and the fall time $Ts2_n$ to the left/right determiner 80.

The moving time calculator 68 executes a calculation of a difference between the fall time $Ts1_n$ and the rise time $Te1_n$ outputted from the timing detector 67, and outputs an execution result thereof as a moving time $\Delta T_n$ to the noise remover 70. Namely, the moving time calculator 68 sequentially outputs the moving time $\Delta T_n$ being a period of time during which the light beam L1 is intercepted by a foot of the subject S, to the noise remover 70.

Figures 4A, 4B:
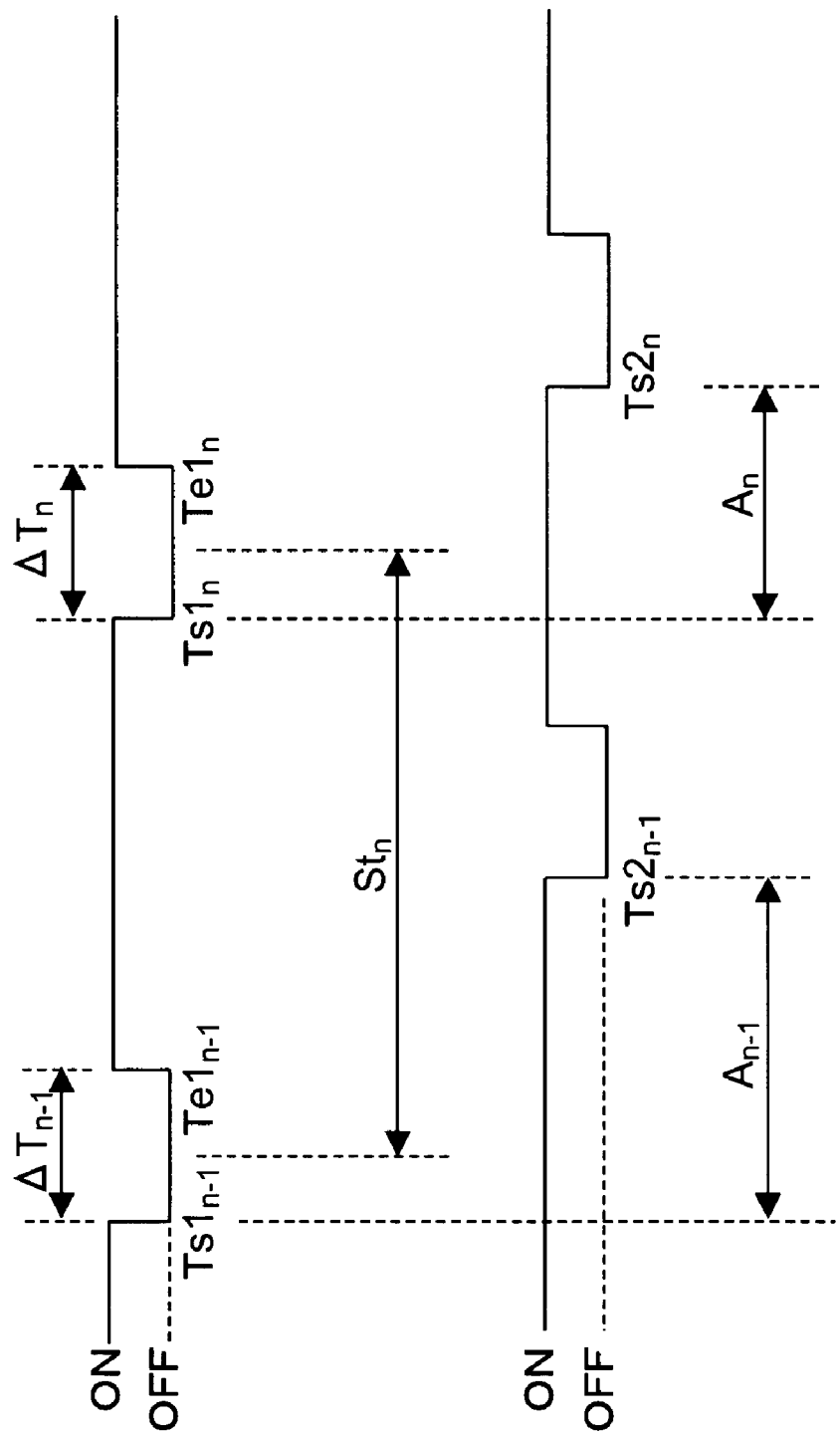
FIG. 4A is a timing chart of signals outputted from a signal wave detector through the states shown in FIG. 3.
FIG. 4B is a timing chart of signals outputted from a second signal wave detector through the states shown in FIG. 3.

For example, supposing the left foot of the subject S passes as indicated by the states D to E in FIG. 3 on the running surface 30, as shown in FIG. 4A, the signal wave detector 62 outputs an OFF signal during a period between $Ts1_n$ and $Te1_n$, i.e., during the period of $\Delta T_n$. The moving time calculator 68 outputs the moving time $\Delta T_n$ being a result of the calculation of the difference between $Ts1_n$ and $Te1_n$, to the noise remover 70.

The noise remover 70 compares the moving time $\Delta T_n$ outputted by the moving time calculator 68, with a moving time outputted at a different time, based on a predetermined rule. When a result of the comparison is that the moving time $\Delta T_n$ is a predetermined amount shorter than the moving time outputted at the different time, the noise remover 70 removes the moving time $\Delta T_n$ as noise. On the other hand, when the result of the same comparison is that the moving time $\Delta T_n$ is not determined to be so shorter, the noise remover 70 outputs the moving time $\Delta T_n$ to the moving speed calculator 72. In the present embodiment, the aforementioned predetermined rule is as follows: the noise remover 70 compares the moving time $\Delta T_n$ with an average time which is an average of several moving times calculated at different times and removes the moving time $\Delta T_n$, for example, when the moving time $\Delta T_n$ is not more than half of the average time. The predetermined rule can be selected from a variety of rules, e.g., the moving time $\Delta T_n$ is compared with an average and a standard deviation of several moving times calculated at different times.

The moving speed calculator 72 performs a calculation of a quotient between the size D of the foot of the subject S and the moving time $\Delta T_n$ outputted from the noise remover 70 and outputs the result of the quotient calculation as a moving speed $V_n$ of the subject S. The moving speed calculator 72 outputs the moving speed $V_n$ to the stride calculator 76 and to the data output part 78.

The stride time calculator 74 executes a calculation of a difference between output times of two OFF signals outputted in succession from the signal wave detector 62 and outputs the result of execution thereof as a stride time $St_n$ to the stride calculator 76 and to the data output part 78. In the present embodiment, the stride time calculator 74 executes a calculation of a difference between an average of a fall time $Ts1_{n-1}$ and a rise time $Te1_{n-1}$ outputted from the timing detector 67 and an average of a fall time $Ts1_n$ and a rise time $Te1_n$ each outputted in succession from the timing detector 67, and outputs the result of execution thereof as the stride time $St_n$. The stride time calculated in this manner is a time that the subject S takes for a step.

For example, when the right foot of the subject S passes as indicated by the states A to B in FIG. 3 on the running surface 30, an OFF signal is outputted between a time $Ts1_{n-1}$ and a time $Te1_{n-1}$ as shown in FIG. 4A and, when the left foot of the subject S passes subsequently thereto as indicated by the states D to E on the running surface 30, an OFF signal is outputted between a time $Ts1_n$ and a time $Te1_n$. The stride time calculator 74 executes a calculation of a difference between an average time of the fall time $Ts1_{n-1}$ and the rise time $Te1_{n-1}$ outputted from the timing detector 67 and an average time of the fall time $Ts1_n$ and the rise time $Te1_n$, and outputs the result of execution thereof as the stride time $St_n$ to the stride calculator 76.

In this manner, the stride time calculator 74 can acquire the stride time $St_n$ with accuracy by the calculation of the difference between the average time of the fall time $Ts1_{n-1}$ and the rise time $Te1_{n-1}$ outputted from the timing detector 67 and the average time of the fall time $Ts1_n$ and the rise time $Te1_n$. The stride time $St_n$ may also be determined from a difference between rise times of two OFF signals outputted in succession by the signal wave detector 62, or from a difference between fall times thereof.

The stride calculator 76 executes a calculation of a product between the moving speed outputted from the moving speed calculator 72 and the stride time outputted from the stride time calculator 74, and determines the result of execution thereof as a stride $W_n$ of the subject S. The stride calculator 76 outputs the calculated stride $W_n$ to the data output part 78. In the present embodiment, the stride calculator 76 determines as the stride $W_n$ a result of a product calculation between the moving speed $V_{n-1}$ outputted from the moving speed calculator 72 and the stride time $St_n$ outputted from the stride time calculator 74.

The left/right determiner 80 determines whether the stride calculated by the stride calculator 76 is a stride of the left foot or the right foot, based on a difference between an output time of an OFF signal outputted by the signal wave detector 62 and an output time of an OFF signal outputted by the second signal wave detector 64.

More specifically, the left/right determiner 80 calculates a time difference $A_{n-1}$ between the fall time $Ts1_{n-1}$ and the fall time $Ts2_{n-1}$ of OFF signals outputted from the timing detector 67, and a time difference $A_n$ between the fall time $Ts1_n$ and the fall time $Ts2_n$ of OFF signals outputted in succession from the timing detector 67. Then the left/right determiner 80 compares the time differences $A_{n-1}$ and $A_n$. When $A_n$ is smaller than $A_{n-1}$ the stride $W_n$ calculated by the stride calculator 76 is determined to be one of the foot closer to the edge part 32, the left foot in the present embodiment. In the reverse case, it is determined to be one of the right foot. The left/right determiner 80 outputs a signal indicating that the stride $W_n$ calculated by the stride calculator 76 is one of the right foot or the left foot, as a result of the determination, to the data output part 78.

For example, when the right foot of the subject S passes as indicated by the states A to C in FIG. 3 on the running surface 30, an OFF signal is outputted from the time $Ts1_{n-1}$ as shown in FIG. 4A, and another OFF signal is further outputted from the time $Ts2_{n-1}$, as shown in FIG. 4B. Subsequently, when the left foot of the subject S passes as indicated by the states D to F in FIG. 3 on the running surface 30, an OFF signal is outputted from the time $Ts1_n$ as shown in FIG. 4A, and another OFF signal is further outputted from the time $Ts2_n$ as shown in FIG. 4B. The left/right determiner 80 compares the time difference $A_{n-1}$ between the fall time $Ts1_{n-1}$ and the fall time $Ts2_{n-1}$ outputted from the timing detector 67 with the time difference An between the fall time $Ts1_n$ and the fall time $Ts2_n$ and determines that $A_n$ is smaller. Then the left/right determiner 80 outputs a signal indicating that the stride $W_n$ calculated by the stride calculator 76 is one of the left foot, to the data output part 78.

Now, the aforementioned predetermined angle of the light beam L2 emitted by the second signal wave emitter 42 will be described. The predetermined angle is an angle enough to enable the left/right determiner 80 to perform the comparison between the first measurement time ($A_{n-1}$) and the second measurement time ($A_n$). More specifically, the predetermined angle θ can be determined as follows. While the subject S is running at 10 km per hour, the subject S moves by about 2.7 cm during the period of 10 ms. Namely, in order to make a difference of 100 ms between the first measurement time and the second measurement time, a necessary difference in the X-direction is approximately 30 cm between a point of an intersection of the right foot with the light beam L2 emitted from the second signal wave emitter 42 and a point of an intersection of the left foot with the light beam L2 emitted from the second signal wave emitter 42. Therefore, where the distance between the second signal wave emitter 42 and the second signal wave detector 64 is 80 cm, the predetermined angle θ is determined to be the angle defined by tanθ=30 cm/80 cm.

The data output part 78 outputs a signal indicating the stride outputted by the stride calculator 76 and the left or right of the stride outputted by the left/right determiner 80, to the computer 90 and to the driving unit for driving the running surface 30 of the treadmill 20.

The computer 90 is physically comprised of a CPU (central processing unit), a storage device such as a memory, an input device such as a keyboard, a display device such as a display, and so on. The computer 90 records information of the moving speed, stride time, and stride fed via a serial interface of RS232C or the like from the stride measuring apparatus 10 and displays variation of stride, variation of moving speed with increase or decrease of stride time, etc. as a graph in real time.

Figure 5:
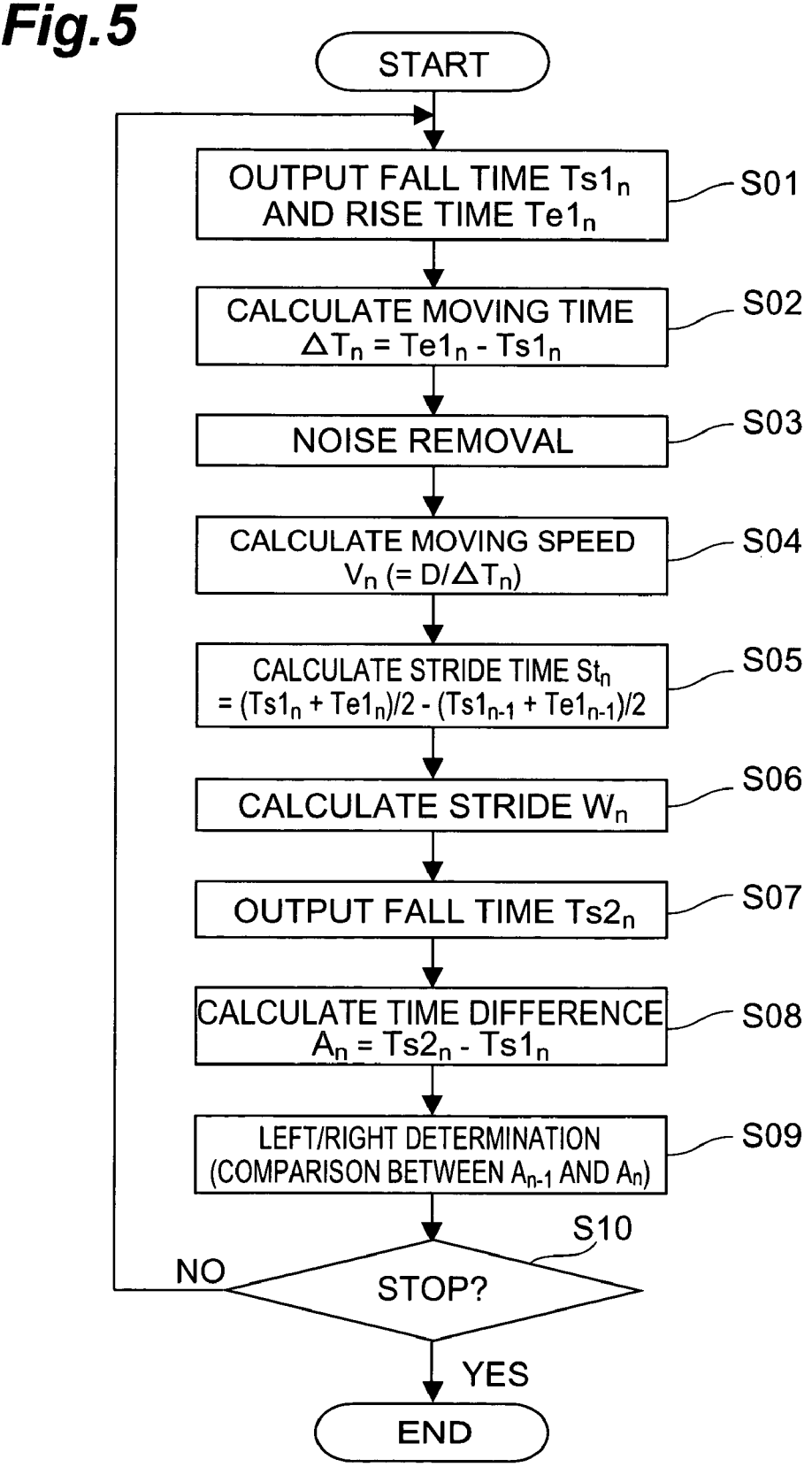
FIG. 5 is a flowchart showing an operation of the detection part in the stride measuring apparatus according to the first embodiment of the present invention.

The operation of the detector part 60 will be described below. FIG. 5 is a flowchart showing the operation of the detector part 60. In FIG. 5, the operation of the detector part 60 is indicated in the order of steps S01 to S10 for convenience' sake, but the operation of the detector part 60 does not have to be limited to the sequence shown in FIG. 5.

As shown in FIG. 5, the timing detector 67 extracts the fall time $Ts1_n$ and the rise time $Te1_n$ of an OFF signal outputted from the signal wave detector 62, and outputs them to the moving time calculator 68 and to the stride time calculator 74. The fall time $Ts1_n$ is also outputted to the left/right determiner 80 (step S01).

Then the moving time calculator 68 sequentially executes the calculation of the difference between the fall time $Ts1_n$ and the rise time $Te1_n$ and outputs the result of execution thereof as the moving time $\Delta T_n$ to the noise remover 70 (step S02).

Then the noise remover 70 removes the moving time $\Delta T_n$ outputted from the moving time calculator 68 if it is determined to be noise as described above. When the moving time $\Delta T_n$ is not determined to be noise, the noise remover 70 outputs the moving time $\Delta T_n$ to the moving speed calculator 72 (step S03).

Then the moving speed calculator 72 executes the calculation of the quotient between the size D of the foot of the subject S and the moving time $\Delta T_n$ outputted from the noise remover 70 and outputs the result of execution thereof as the moving speed $V_n$ of the subject S to the stride calculator 76 and to the data output part 78 (step S04).

Next, the stride time calculator 74 executes the calculation of the difference between the average time of the fall time $Ts1_{n-1}$ and the rise time $Te1_{n-1}$ outputted from the timing detector 67 and the average time of the fall time $Ts1_n$ and the rise time $Te1_n$ outputted in succession from the timing detector 67, and outputs the result of execution thereof as the stride time $St_n$ to the stride calculator 76 and to the data output part 78 (step S05).

Subsequently, the stride calculator 76 executes the calculation of the product between the moving speed $V_{n-1}$ outputted by the moving speed calculator 72, and the stride time $St_n$ and outputs the result of execution thereof as the stride $W_n$ of the subject S to the data output part 78 (step S06).

Next, the timing detector 67 extracts the fall time $Ts2_n$ of an OFF signal outputted from the second signal wave detector 64 and outputs it to the left/right determiner 80 (step S07). The left/right determiner 80 calculates the time difference $A_n$ between the fall time $Ts2_n$ and the fall time $Ts1_n$ (step S08) and compares the time difference $A_n$ with the time difference $A_{n-1}$ previously determined, thereby determining whether the stride $W_n$ outputted by the stride calculator 76 is one of the left foot or the right foot. The left/right determiner 80 outputs a signal indicating the left foot or the right foot according to the result of the determination, to the data output part 78 (step S09).

The data output part 78 outputs the moving speed $V_n$ of the subject S, the stride time $St_n$, and the stride $W_n$ to the computer 90, to the driving unit of the treadmill 20, and so on. The computer 90 displays the newly calculated stride $W_n$ on a time-varying graph of stride, and the driving unit of the treadmill 20 adjusts the driving speed of the running surface 30 according to the moving speed $V_n$ of the subject S and the stride time $St_n$.

Subsequently, it is determined whether the operation of the treadmill 20 is stopped by the subject S (step S10). When it is stopped, the operation of the detector part 60 is terminated. When it is not stopped on the other hand, the sequential operation from step S01 is repeated.

As described above, the stride measuring apparatus 10 of the present embodiment is able to measure the stride of the subject S by the configuration wherein the signal wave emitter 40 is provided on the cover 28 along one edge part 32 of the running surface 30 and the signal wave detector 62 on the other edge part 34, as a sensor. Therefore, the present embodiment provides the compact stride measuring apparatus. The stride measuring apparatus 10 of the present embodiment is able to calculate the moving speed of the subject S, without using the driving speed of the belt.

Furthermore, the stride measuring apparatus 10 of the present embodiment is able to determine whether the calculated stride is one of the left foot or the right foot, by making use of the fact that a period of time between an intercept of the light beam L1 and an intercept of the light beam L2 by the left foot is different from that by the right foot.

In order to circumvent crosstalk, it is also possible to adopt a configuration wherein the signal wave emitter 40 is placed at a position along the other edge part 34 of the treadmill 20 while the signal wave detector 62 is placed at a position along one edge part 32 of the treadmill 20. It is also possible to adopt another configuration wherein the second signal wave emitter 42 is placed at a position along the other edge part 34 of the treadmill 20 while the second signal wave detector 64 is placed at a position along one edge part 32 of the treadmill 20.

The wavelengths of the signal wave L1 emitted by the signal wave emitter 40 and the second signal wave L2 emitted by the second signal wave emitter 42 may be equal to or different from each other. The signal wave L1 and the second signal wave L2 may be optical pulses, and frequencies thereof may be equal to or different from each other.

Figure 6:
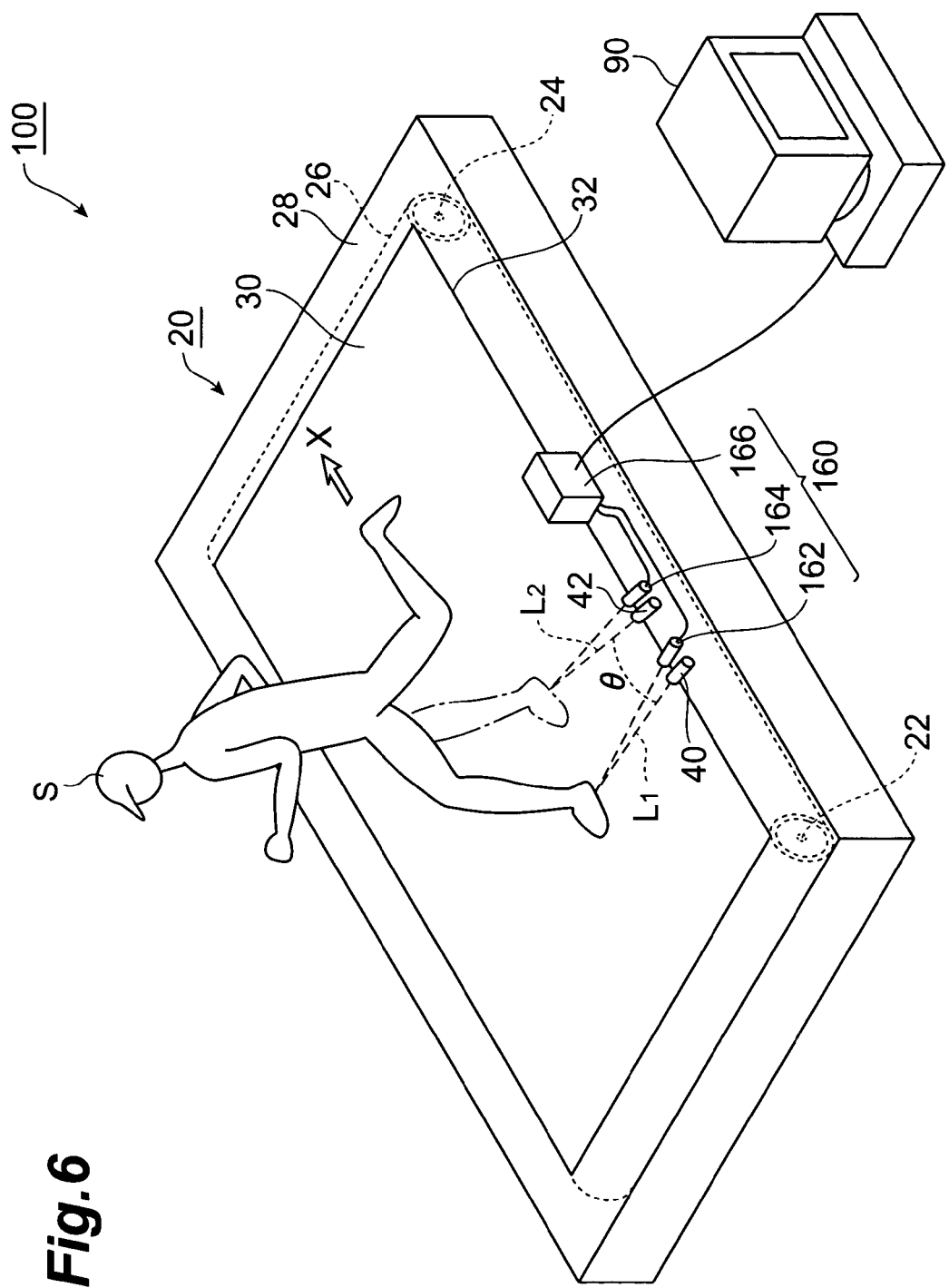
FIG. 6 is a perspective view schematically showing a stride measuring apparatus according to the second embodiment of the present invention.

A stride measuring apparatus 100 according to the second embodiment of the present invention will be described below. FIG. 6 is a perspective view schematically showing the stride measuring apparatus according to the second embodiment of the present invention. The stride measuring apparatus 100 shown in FIG. 6 has a treadmill 20, a signal wave emitter 40 (signal wave emitting means), a second signal wave emitter (second signal wave emitting means) 42, and a computer 90 similar to those in the stride measuring apparatus 10 of the first embodiment. The stride measuring apparatus 100 is further provided with a detector part 160. The detector part 160 different in structure from that in the stride measuring apparatus 10 of the first embodiment will be described below.

The detector part 160 has a signal wave detector 162 (signal wave detecting means), a second signal wave detector 164 (second signal wave detecting means), and a calculation part 166. The signal wave detector 162 is placed at a position along one edge part 32 of the treadmill 20, i.e., on the cover 28 extending along the edge part 32 and is configured to receive reflected light of the light beam L1 emitted from the signal wave emitter 40 and reflected by a foot of the subject S. The signal wave detector 162 outputs an ON signal as a first signal to the calculation part 166 when the reflected light of the light beam L1 is received. The signal wave detector 162 outputs an OFF signal as a second signal to the calculation part 166 when no reflected light is received.

The second signal wave detector 164 is placed at a position along one edge part 32 of the treadmill 20, i.e., on the cover 28 extending along the edge part 32 and is configured to receive reflected light of the light beam L2 emitted from the second signal wave emitter 42 and reflected by a foot of the subject S. When receiving the reflected light of the light beam L2, the second signal wave detector 164 outputs an ON signal as a first signal to the calculation part 166. When receiving no reflected light, the second signal wave detector 164 outputs an OFF signal as a second signal to the calculation part 166.

As described above, the signal wave detector 162 and the second signal wave detector 164 output an ON signal as a first signal to the calculation part 166. The calculation part 166 executes a process for determining the stride on the basis of ON signals respectively outputted from the signal wave detector 162 and from the second signal wave detector 164. Therefore, the process for the calculation part 166 to determine the stride is different from that by the calculation part 66 in the first embodiment only in that the rise time and fall time are reverse, and is thus similar in the other processing to that by the calculation part 66 in the first embodiment. The components are also much the same and thus the description of the calculation part 166 is omitted herein.

As described above, it is also feasible to determine the stride of the subject S, using the reflected light of the light beam L1 reflected by the feet of the subject S. It is also feasible to determine whether the stride of the subject S is one of the left foot or the right foot, using the reflected light of the light beam L2 reflected by the feet of the subject S.

Figure 7:
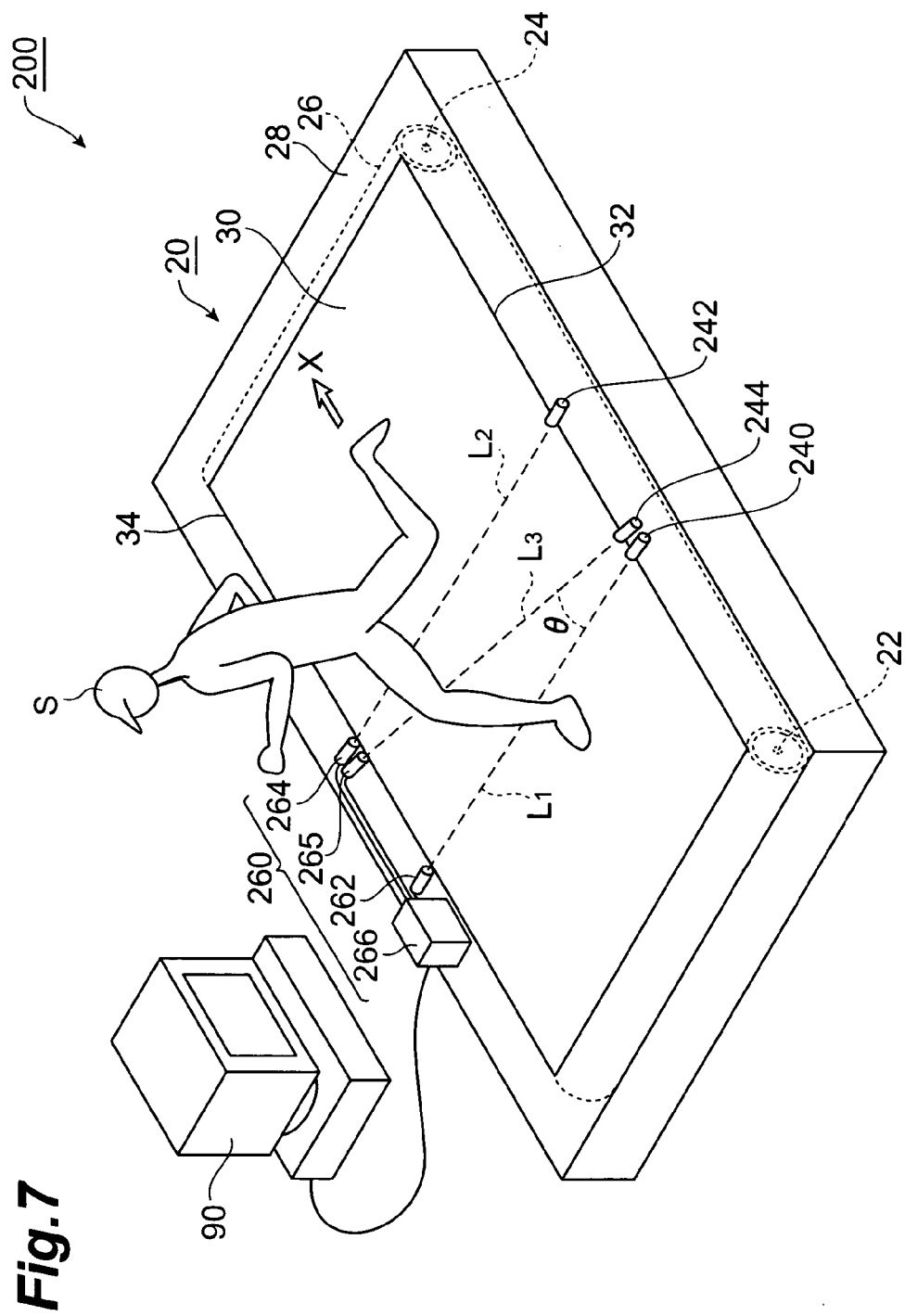
FIG. 7 is a perspective view schematically showing a stride measuring apparatus according to the third embodiment of the present invention.

Next, a stride measuring apparatus 200 according to the third embodiment of the present invention will be described. FIG. 7 is a perspective view schematically showing the stride measuring apparatus according to the third embodiment of the present invention. The stride measuring apparatus 200 shown in FIG. 7 has a treadmill 20 and a computer 90 similar to those in the stride measuring apparatus 10 of the first embodiment. Furthermore, the stride measuring apparatus 200 has a first signal wave emitter 240 (first signal wave emitting means), a second signal wave emitter 242 (second signal wave emitting means), a third signal wave emitter 244 (third signal wave emitting means), and a detector part 260.

The first signal wave emitter 240 is placed at a position along one edge part 32 of the treadmill 20 and is configured to emit a first signal wave L1 in a direction intersecting with the predetermined direction in which the running surface 30 of the treadmill 20 is driven (reference symbol X in FIG. 9) and at a predetermined height relative to the running surface. In the present embodiment, the first signal wave emitter 240 is a light source to emit a light beam L1 as the first signal wave L1 and is placed on the cover 28 extending along the edge part 32. The emission direction of the light beam L1 is a direction substantially perpendicular to the aforementioned predetermined direction. The predetermined height is a height similar to that in the first embodiment.

The second signal wave emitter 242 is placed a predetermined distance D apart in the aforementioned predetermined direction from the position where the first signal wave emitter 240 is located. The second signal wave emitter 242 is configured to emit a second signal wave L2 in a direction intersecting with the predetermined direction and at a predetermined height relative to the running surface 30. In the present embodiment, the second signal wave emitter 242 is a light source to emit a light beam L2 as the second signal wave L2 and is placed on the cover 28 extending along the edge part 32. The emission direction of the light beam L2 and the height relative to the running surface 30 are similar to those of the light beam L1. The predetermined distance D is a distance acquired in consideration of the stride of the subject S and is, for example, a distance of 10–15 cm where the stride of the subject S is 60 cm.

The third signal wave emitter 244 is placed at a position along one edge part 32 of the treadmill 20. The third signal wave emitter 244 is configured to emit a third signal wave L3. In the present embodiment, the third signal wave emitter 244 is a light source to emit a light beam L3 as the third signal wave L3 and is placed on the cover 28 extending along the edge part 32. The predetermined height, i.e., the height at which the light beam L3 passes relative to the running surface 30, is similar to that of the light beam L1. The third signal wave emitter 244 emits the light beam L3 so as to be inclined at a predetermined angle relative to the emission direction of the light beam L1. This predetermined angle is similar to the angle between the emission directions of the respective light beams L1 and L2 in the first embodiment.

The detector part 260 has a first signal wave detector 262 (first signal wave detecting means), a second signal wave detector 264 (second signal wave detecting means), a third signal wave detector 265 (third signal wave detecting means), and a calculation part 266.

The first signal wave detector 262 is placed at a position along the other edge part 34 of the treadmill 20 and opposite the first signal wave emitter 240 and is configured to detect the first signal wave L1 emitted by the first signal wave emitter 240. In the present embodiment, the first signal wave detector 262 is equipped with a light receiving device for receiving the light beam L1, and is placed on the cover 28 extending along the edge part 34. The first signal wave detector 262 outputs an OFF signal as a first signal when the light beam L1 is intercepted, and outputs an ON signal as a second signal when detecting the light beam L1, each to the calculation part 266.

The second signal wave detector 264 is placed at a position along the other edge part 34 of the treadmill 20 and opposite the second signal wave emitter 242 and is configured to detect the second signal wave L2 emitted by the second signal wave emitter 242. In the present embodiment, the second signal wave detector 264 is equipped with a light receiving device for receiving the light beam L2 and is placed on the cover 28 extending along the edge part 34. The second signal wave detector 264 outputs an OFF signal as a first signal when the light beam L2 is intercepted, and outputs an ON signal as a second signal when detecting the light beam L2, each to the calculation part 266.

The third signal wave detector 265 is placed at a position along the other edge part 34 of the treadmill 20 so as to detect the third signal wave L3. In the present embodiment, the third signal wave detector 265 is equipped with a light receiving device for receiving the light beam L3, and is placed on the cover 28 extending along the edge part 34. The third signal wave detector 265 outputs an OFF signal as a first signal when receiving the light beam L3 from the third signal wave emitter 244, and outputs an ON signal as a second signal when the light beam L3 is intercepted, to the calculation part 266.

Figure 8:
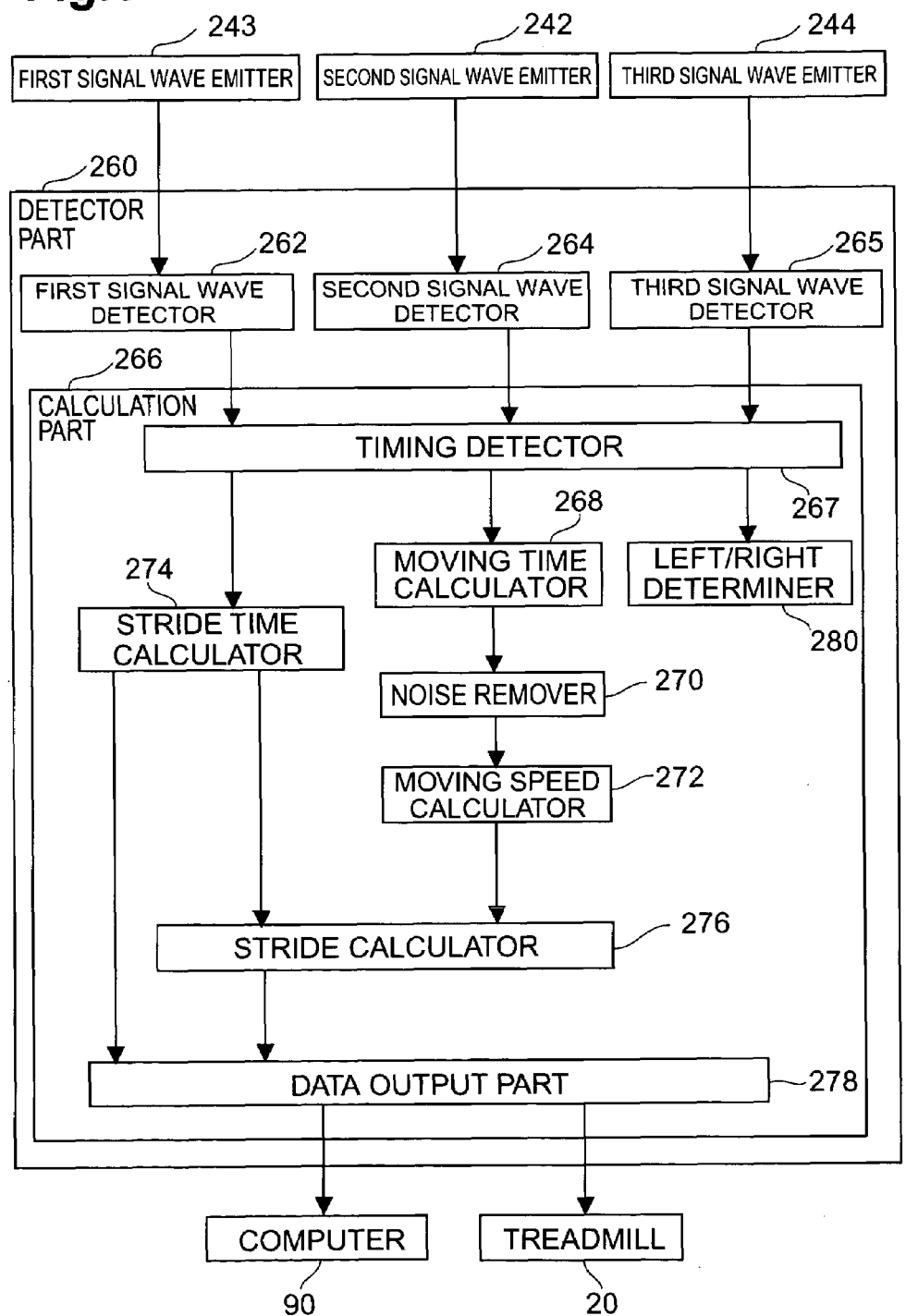
FIG. 8 is an illustration showing a configuration of a detector part according to the third embodiment of the present invention.

The calculation part 266 will be described below in detail. FIG. 8 is an illustration showing a configuration of the calculation part 266. The calculation part 266 has a timing detector 267, a moving time calculator 268 (moving time calculating means), a noise remover 270 (noise removing means), a moving speed calculator 272 (moving speed calculating means), a stride time calculator 274 (stride time calculating means), a stride calculator 276 (stride calculating means), a data output part 278, and a left/right determiner 280 (left/right determining means).

The components of the calculation part 266 will be described below in detail with reference to FIG. 9 showing states in which the feet of the subject S running on the running surface pass across the light beams L1, L2, and L3 with the passage of time, FIG. 10A being a timing chart of signals outputted from the first signal wave detector 262 through the states A to J shown in FIG. 9, FIG. 10B being a timing chart of signals outputted from the third signal wave detector 265 in similar fashion, and FIG. 10C being a timing chart of signals outputted from the second signal wave detector 264 in similar fashion. In the description below, subscripts n-1 and n will be used in order to indicate a sequence of time.

The timing detector 267 extracts a fall time $Ts1_n$ and a rise time $Te1_n$ of an OFF signal outputted from the first signal wave detector 262 and a fall time $Ts2_n$ and a rise time $Te2_n$ of an OFF signal outputted from the second signal wave detector 264, and outputs them to the moving speed calculator 272 and to the stride time calculator 274. The timing detector 267 also extracts a fall time $Ts3_n$ of an OFF signal outputted from the third signal wave detector 265 and outputs $Ts3_n$ along with the fall times $Ts1_n$ and $Ts2_n$ to the left/right determiner 280.

The moving time calculator 268 in the present embodiment executes a calculation of a difference between the fall time $Ts1_n$ and the fall time $Ts2_n$ outputted by the timing detector 267 and outputs the result of execution thereof as a moving time $\Delta Ts_n$ to the noise remover 270. The moving time calculator 268 also executes a calculation of a difference between the rise time $Te1_n$ and the rise time $Te2_n$ outputted by the timing detector 267 and outputs the result of execution thereof as a moving time $\Delta Te_n$ to the noise remover. Namely, the moving time calculator 268 sequentially outputs to the noise remover 270 the moving time which is a period of time between an intercept of the light beam L1 and an intercept of the light beam L2 by a foot of the subject S.

Figures 10A, 10B, 10C:
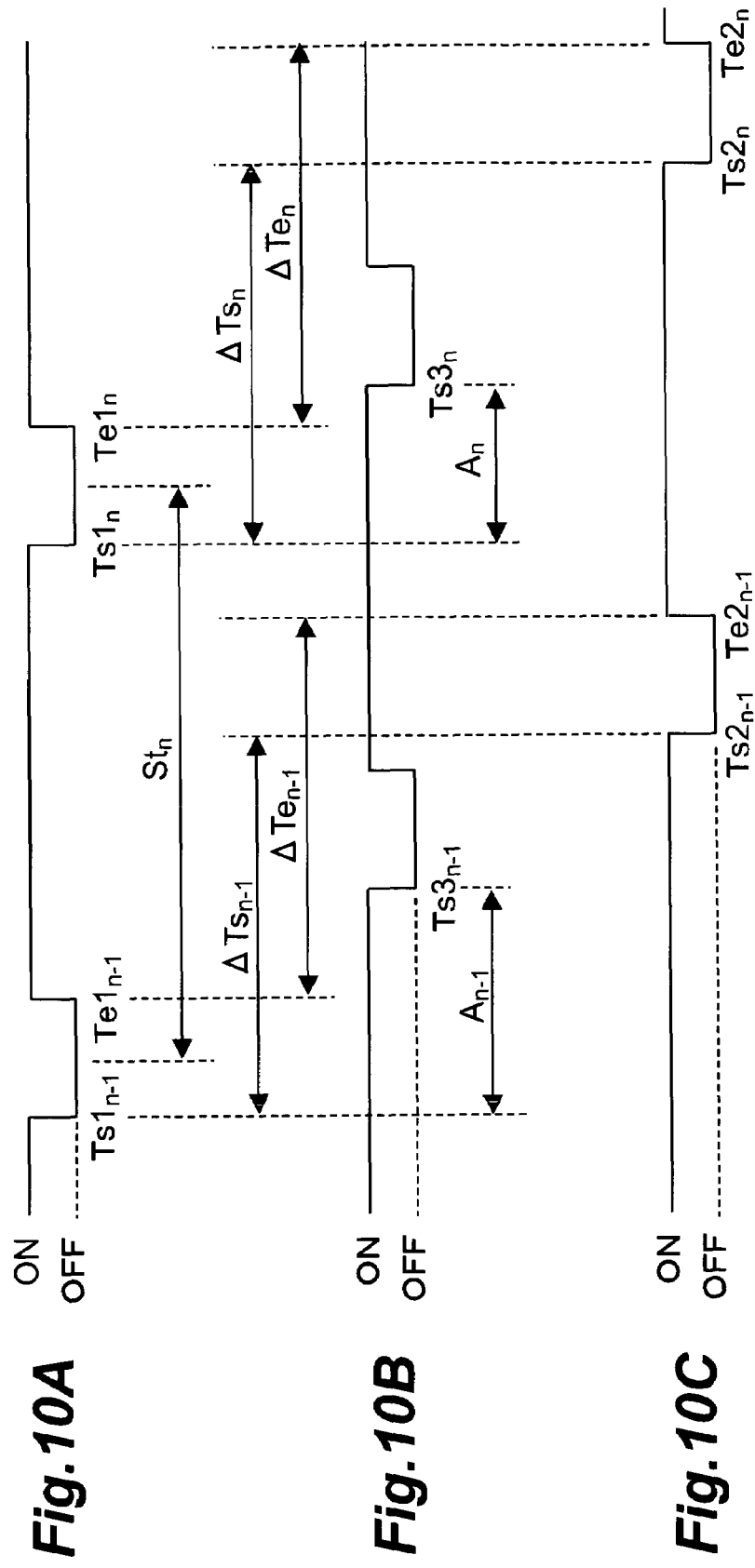
FIG. 10A is a timing chart of signals outputted from a first signal wave detector through the states shown in FIG. 9.
FIG. 10B is a timing chart of signals outputted from a third signal wave detector through the states shown in FIG. 9.
FIG. 10C is a timing chart of signals outputted from a second signal wave detector through the states shown in FIG. 9.

For example, supposing the right foot of the subject S passes as indicated by the states F to J in FIG. 9 on the running surface 30, as shown in FIG. 10A, the first signal wave detector 262 outputs an OFF signal between $Ts1_n$ and $Te1_n$. The second signal wave detector 264 outputs an OFF signal between $Ts2_n$ and $Te2_n$ as shown in FIG. 10C. The moving time calculator 268 outputs to the noise remover 270 the moving time $\Delta Ts_n$ being the result of the difference calculation between $Ts1_n$ and $Ts2_n$ and the moving time $\Delta Te_n$ being the result of the difference calculation between $Te1_n$ and $Te2_n$.

In the present embodiment, the moving time calculator 268 outputs $\Delta Ts_n$ and $\Delta Te_n$ as moving times to the noise remover 270, but may be configured to output either one of them.

The noise remover 270, similar to the noise remover 70 in the first embodiment, removes a moving time determined to be noise, out of moving times outputted from the moving time calculator 268 and also outputs a moving time not determined to be noise, to the moving speed calculator 272. Since the process by the noise remover 270 is similar to that by the noise remover 70 described in the first embodiment, the detailed description thereof is omitted herein.

The moving speed calculator 272 executes a calculation of a quotient between the predetermined distance D between the first signal wave emitter 240 and the second signal wave emitter 242 and the moving time outputted from the noise remover 270, and outputs the result of execution thereof as a moving speed $V_n$ of the subject S to the stride calculator 276. In the present embodiment, the moving speed calculator 272 outputs as the moving speed $V_n$ an average of a moving speed $Vs_n$ obtained by a quotient calculation between the predetermined distance D and the moving time $\Delta Ts_n$ outputted from the noise remover 270 and a moving speed $Ve_n$ obtained by a quotient calculation between the predetermined distance D and the moving time $\Delta Te_n$, to the stride calculator 276. The moving speed calculator 272 may determined one of the above moving speed $Vs_n$ and moving speed $Ve_n$ as the moving speed $V_n$.

The stride time calculator 274 executes a calculation of a difference between output times of two OFF signals outputted in succession from one of the first signal wave detector 262 and the second signal wave detector 264, and outputs the result of execution thereof as a stride time $St_n$ to the stride calculator 276 and to the data output part 278.

In the present embodiment, the stride time calculator 274 executes a calculation of a difference between an average of the fall time $Ts1_{n-1}$ and rise time $Te1_{n-1}$ outputted from the timing detector 267 and an average of the fall time $Ts1_n$ and rise time $Te1_n$ each outputted in succession from the timing detector 267, and defines the result of execution thereof as the stride time $St_n$. The stride time $St_n$ calculated in this way is a time that the subject S takes for a step.

For example, supposing the right foot of the subject S passes as indicated by the states A to B in FIG. 9 on the running surface 30, as shown in FIG. 10A, an OFF signal is outputted during the period from the time $Ts1_{n-1}$ to the time $Te1_{n-1}$, and, when the left foot of the subject S subsequently passes as indicated by the states F to G on the running surface 30, an OFF signal is outputted during a period between the time $Ts1_n$ and the time $Te1_n$. The stride time calculator 274 executes a calculation of a difference between an average time of the fall time $Ts1_{n-1}$ and rise time $Te1_{n-1}$ outputted from the timing detector 267 and an average time of the fall time $Ts1_n$ and rise time $Te1_n$, and outputs the result of execution thereof as the stride time $St_n$ to the stride calculator 276.

In this manner, the stride time calculator 274 is able to determine the stride time $St_n$ with accuracy by the difference calculation between the average time of the fall time $Ts1_{n-1}$ and rise time $Te1_{n-1}$ outputted from the timing detector 267 and the average time of the fall time $Ts1_n$ and rise time $Te1_n$. The stride time $St_n$ may also be determined from the difference between the fall times $Ts1_{n-1}$ and $Ts1_n$ or from the difference between the rise times $Te1_{n-1}$ and $Te1_n$.

The stride calculator 276 executes a calculation of a product between the moving speed outputted from the moving speed calculator 272 and the stride time outputted from the stride time calculator 274 and defines the result of execution thereof as a stride $W_n$ of the subject S. The stride calculator 276 outputs the calculated stride $W_n$ to the data output part 278. In the present embodiment, the stride calculator 276 determines the result of the product calculation between the moving speed $V_{n-1}$ outputted from the moving speed calculator 272 and the stride time $St_n$ outputted from the stride time calculator 274, as the stride $W_n$.

The left/right determiner 280 determines whether the stride calculated by the stride calculator 276 is one of the left foot or the right foot, based on a difference between an output time of an OFF signal outputted from one of the first signal wave detector 262 and the second signal wave detector 264 and an output time of an OFF signal outputted from the third signal wave detector 265.

More specifically, in the present embodiment the left/right determiner 280 calculates the time difference $A_{n-1}$ between the fall time $Ts1_{n-1}$ and the fall time $Ts3_{n-1}$ of OFF signals outputted from the timing detector 267, and the time difference $A_n$ between the fall time $Ts1_n$ and the fall time $Ts3_n$ of OFF signals outputted in succession from the timing detector 267. Then the left/right determiner 280 compares the time differences $A_{n-1}$ and $A_n$. When $A_n$ is smaller than $A_{n-1}$, the stride $W_n$ calculated by the stride calculator 276 is determined to be one of the foot closer to the edge part 32, the left foot in the present embodiment. In the reverse case, it is determined to be one of the right foot. The left/right determiner 280 outputs the result of the determination, a signal indicating that the stride $W_n$ calculated by the stride calculator 276 is one of the right foot or the left foot, to the data output part 278. Since the data output part 278 has a configuration similar to that of the data output part 78 in the first embodiment, the description thereof is omitted herein.

Figure 11:
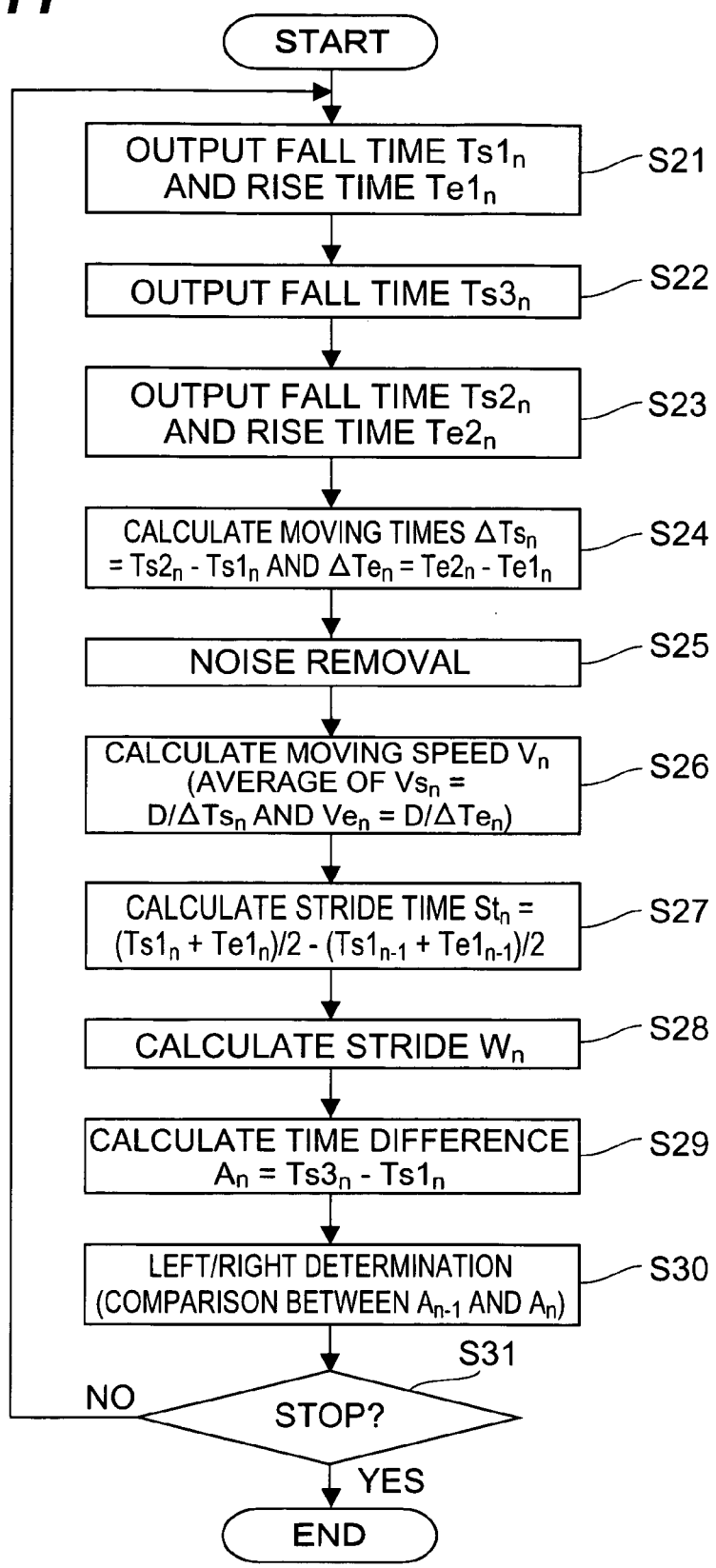
FIG. 11 is a flowchart showing an operation of a detector part in the stride measuring apparatus according to the third embodiment of the present invention.

The operation in the detector part 260 of the stride measuring apparatus 200 will be described below with reference to the flowchart of FIG. 11. FIG. 11 shows the operation of the detector part 260 in the order of steps S21 to S31 for convenience' sake, but the operation of the detector part 260 does not have to be limited to the sequence shown in FIG. 11.

As shown in FIG. 11, the timing detector 267 extracts the fall time $Ts1_n$ and rise time $Te1_n$ of an OFF signal outputted from the first signal wave detector 262, and outputs them to the moving time calculator 268 and to the stride time calculator 274. The fall time $Ts1_n$ is also outputted to the left/right determiner 280 (step S21).

Then the timing detector 267 extracts the fall time $Ts3_n$ of the OFF signal outputted from the third signal wave detector 265 and outputs it to the left/right determiner 280 (step S22).

Next, the timing detector 267 extracts the fall time $Ts2_n$ and rise time $Te2_n$ of an OFF signal outputted from the second signal wave detector 264 and outputs them to the moving time calculator 268 and to the stride time calculator 274 (step S23).

Next, the moving time calculator 268 sequentially executes the difference calculation between the fall time $Ts1_n$ and the fall time $Ts2_n$ and the difference calculation between the rise time $Te1_n$ and the rise time $Te2_n$, and outputs the results of execution as moving times $\Delta Ts_n$, $\Delta Te_n$ each to the noise remover 270 (step S24).

Subsequently, the noise remover 270 removes a moving time determined to be noise as described above, out of the moving times $\Delta Ts_n$, $\Delta Te_n$ outputted by the moving time calculator 268. When they are not determined to be noise, the moving times $\Delta Ts_n$, $\Delta Te_n$ are outputted to the moving speed calculator 272 (step S25).

Subsequently, the moving speed calculator 272 executes the quotient calculations between the predetermined distance D and the moving times $\Delta Ts_n$, $\Delta Te_n$ outputted from the noise remover 270 to calculate the moving speeds $Vs_n$, $Ve_n$, and outputs an average of $Vs_n$ and $Ve_n$ as a moving speed $V_n$ to the stride calculator 276 and to the data output part 278 (step S26).

Next, the stride time calculator 274 executes the difference calculation between the average time of the fall time $Ts1_{n-1}$ and rise time $Te1_{n-1}$ outputted from the timing detector 267 and the average time of the fall time $Ts1_n$ and rise time $Te1_n$ outputted in succession from the timing detector 267, and outputs the result of execution thereof as a stride time $St_n$ to the stride calculator 276 and to the data output part 278 (step S27).

Then the stride calculator 276 executes the product calculation between the moving speed $V_{n-1}$ outputted from the moving speed calculator 272 and the stride time $St_n$ and outputs the result of execution thereof as a stride $W_n$ of the subject S to the data output part 278 (step S28).

Then the left/right determiner 280 calculates the time difference $A_n$ between the fall time $Ts3_n$ and the fall time $Ts1_n$ (step S29) and compares the time difference $A_n$ with the time difference $A_{n-1}$ obtained previously, thereby determining whether the stride $W_n$ outputted by the stride calculator 276 is one of the left foot or the right foot. The left/right determiner 280 outputs a signal indicating the left foot or the right foot, according to the result of the determination, to the data output part 278 (step S30).

The data output part 278 outputs the moving speed $V_n$ of the subject S, the stride time $St_n$, and the stride $W_n$ to the computer 90, to the driving unit of the treadmill 20, and so on. The computer 90 displays the newly calculated stride $W_n$ on a time-varying graph of stride, and the driving unit of the treadmill 20 adjusts the driving speed of the running surface 30 according to the moving speed $V_n$ of the subject S and the stride time $St_n$.

Subsequently, it is detected whether the operation of the treadmill 20 is stopped by the subject S (step S31). When it is stopped, the operation of the detector part 260 is terminated. On the other hand, when it is not stopped, the sequential operation from step S21 is repeated.

As described above, the stride measuring apparatus 200 of the present embodiment is able to measure the stride of the subject S by the configuration wherein the first signal wave emitter 240 and the second signal wave emitter 242 are provided on the cover 28 along one edge part 32 of the running surface 30 and the first signal wave detector 262 and the second signal wave detector 264 along the other edge part 34, as a sensor. Therefore, the present embodiment provides the compact stride measuring apparatus. The stride measuring apparatus 200 of the present embodiment is also able to calculate the moving speed of the subject S, without using the driving speed of the belt.

Furthermore, the stride measuring apparatus 200 of the present embodiment is able to determine whether the calculated stride is one of the left foot or the right foot, utilizing the fact that the period of time between an intercept of the light beam L1 and an intercept of the light beam L3 by the left foot is different from that by the right foot.

In order to circumvent crosstalk, it is also possible to adopt a configuration wherein the first signal wave emitter 240 and the second signal wave emitter 242 are placed at positions along the other edge part 34 of the treadmill 20 while the first signal wave detector 262 and the second signal wave detector 264 are placed at positions along one edge part 32 of the treadmill 20. Another potential configuration is such that the third signal wave emitter 244 is placed at a position along the other edge part 34 of the treadmill 20 while the third signal wave detector 265 is placed at a position along one edge part 32 of the treadmill 20.

The wavelengths of the first signal wave L1 emitted by the first signal wave emitter 240, the second signal wave L2 emitted by the second signal wave emitter 242, and the third signal wave L3 emitted by the third signal wave emitter 244 may be equal to or different from each other. The first signal wave L1, the second signal wave L2, and the third signal wave L3 may be optical pulses and frequencies thereof may be equal to or different from each other.

Figure 12:
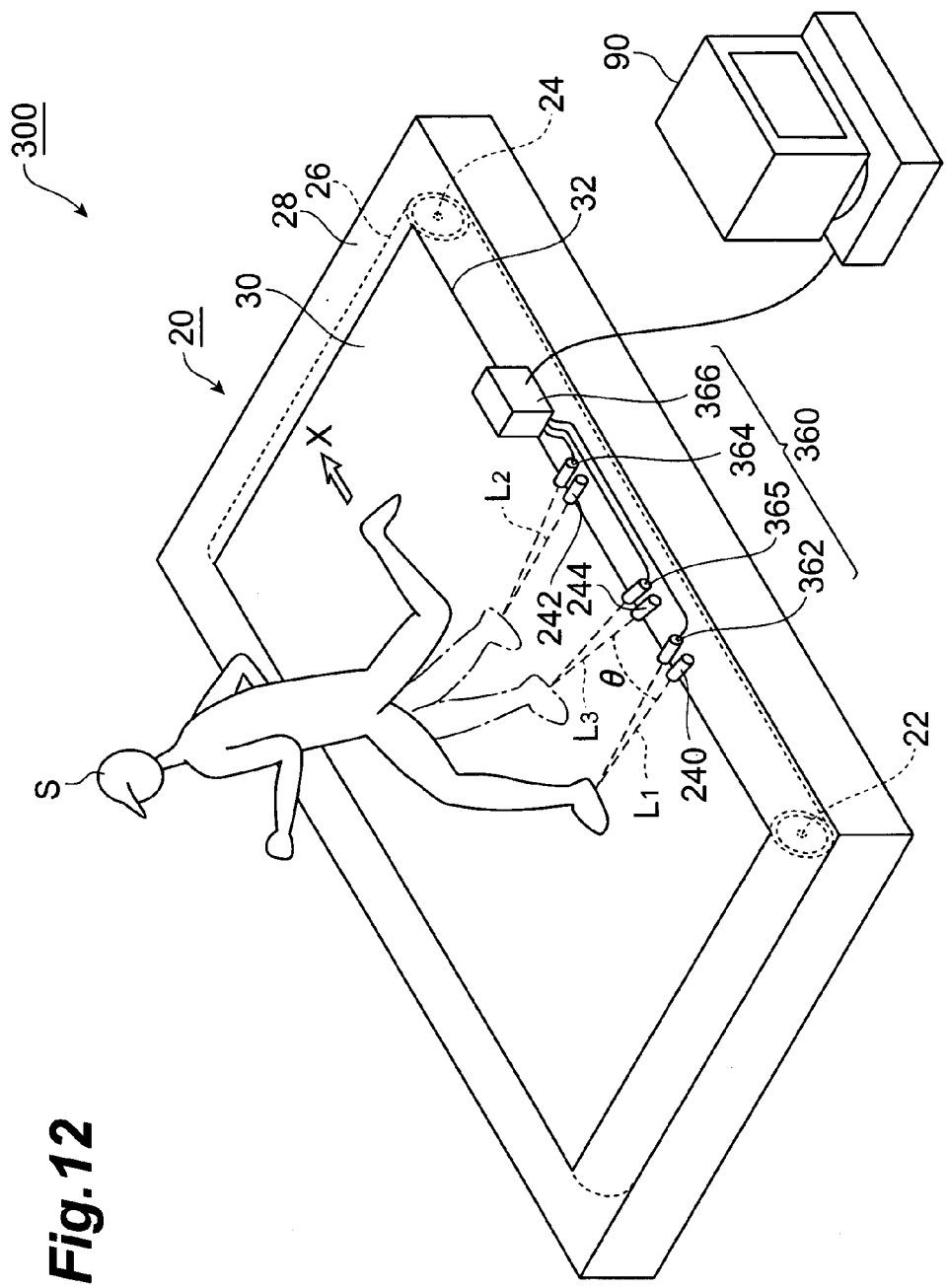
FIG. 12 is a perspective view schematically showing a stride measuring apparatus according to the fourth embodiment of the present invention.

Next, a stride measuring apparatus 300 according to the fourth embodiment of the present invention will be described. FIG. 12 is a perspective view schematically showing the stride measuring apparatus according to the fourth embodiment of the present invention. The stride measuring apparatus 300 shown in FIG. 12 has a treadmill 20 and a computer 90 similar to those in the stride measuring apparatus 10 of the first embodiment, and a first signal wave emitter 240 (first signal wave emitting means), a second signal wave emitter 242 (second signal wave emitting means), and a third signal wave emitter 244 (third signal wave emitting means) similar to those in the third embodiment. The stride measuring apparatus 100 further has a detector part 360. The detector part 360 different in structure from that in the stride measuring apparatus 10 of the first embodiment and from that in the stride measuring apparatus 200 of the third embodiment will be described below.

The detector part 360 has a first signal wave detector 362 (first signal wave detecting means), a second signal wave detector 364 (second signal wave detecting means), a third signal wave detector 365 (third signal wave detecting means), and a calculation part 366.

The first signal wave detector 362 is placed at a position along one edge part 32 of the treadmill 20, i.e., on the cover 28 extending along the edge part 32, and is configured to receive reflected light of a light beam L1 emitted from the signal wave emitter 240 and reflected by a foot of subject S. The first signal wave detector 362 outputs an ON signal as a first signal when receiving the reflected light of the light beam L1, and outputs an OFF signal as a second signal when not receiving the reflected light, to the calculation part 366.

The second signal wave detector 364 is placed at a position along one edge part 32 of the treadmill 20, i.e., on the cover 28 extending along the edge part 32, and is configured to receive reflected light of a light beam L2 emitted from the second signal wave emitter 242 and reflected by a foot of subject S. The second signal wave detector 364 outputs an ON signal as a first signal when receiving the reflected light of the light beam L2, and outputs an OFF signal as a second signal when not receiving the reflected light, to the calculation part 366.

The third signal wave detector 365 is placed at a position along one edge part 32 of the treadmill 20, i.e., on the cover 28 extending along the edge part 32, and is configured to receive reflected light of a light beam L3 emitted from the third signal wave emitter 244 and reflected by a foot of subject S. The third signal wave detector 365 outputs an ON signal as a first signal when receiving the reflected light of the light beam L3, and outputs an OFF signal as a second signal when not receiving the reflected light, to the calculation part 366.

As described above, the first signal wave detector 362, the second signal wave detector 364, and the third signal wave detector 365 output an ON signal as a first signal to the calculation part 366. The calculation part 366 executes a process for determining a stride on the basis of ON signals respectively outputted from the first signal wave detector 362, from the second signal wave detector 364, and from the third signal wave detector 365. Therefore, the process for the calculation part 366 to determine a stride is much the same as that by the calculation part 266 in the third embodiment, except that the rise time and fall time are reverse. In addition, the components are also similar and therefore the description of the calculation part 366 is omitted herein.

As described above, a stride of the subject S can also be determined by using the reflected light of the light beam L1 and the reflected light of the light beam L2 reflected by the foot of the subject S. It is also feasible to determine whether the stride of the subject S is one of the left foot or the right foot, using the reflected light of the light beam L3 reflected by the foot of the subject S.

The first to fourth embodiments of the present invention were described above, and it is noted that a variety of modification examples of the present invention can be constructed without being limited to the above embodiments. For example, in order to free the subject S from constraints on landing positions on the running surface 30, a plurality of signal wave emitters and signal wave detectors may be installed. This permits a time of an intersection between a foot of the subject S and an optical beam to be selected from outputs from the signal wave detectors, whereby a stride can be calculated no matter where the subject S lands.

The signal wave emitter 40, second signal wave emitter 42, first signal wave emitter 240, second signal wave emitter 242, and third signal wave emitter 244 may be equipped with a transmitter that emits an ultrasonic wave or a radio wave or the like, instead of the light beam. In accordance therewith, a detector for receiving an ultrasonic wave or a radio wave or the like can be used in the signal wave detector 62, the second signal wave detector 64, the signal wave detector 162, the second signal wave detector 164, the first signal wave detector 262, the second signal wave detector 264, the third signal wave detector 265, the first signal wave detector 362, the second signal wave detector 364, and the third signal wave detector 365.

Figure 13:
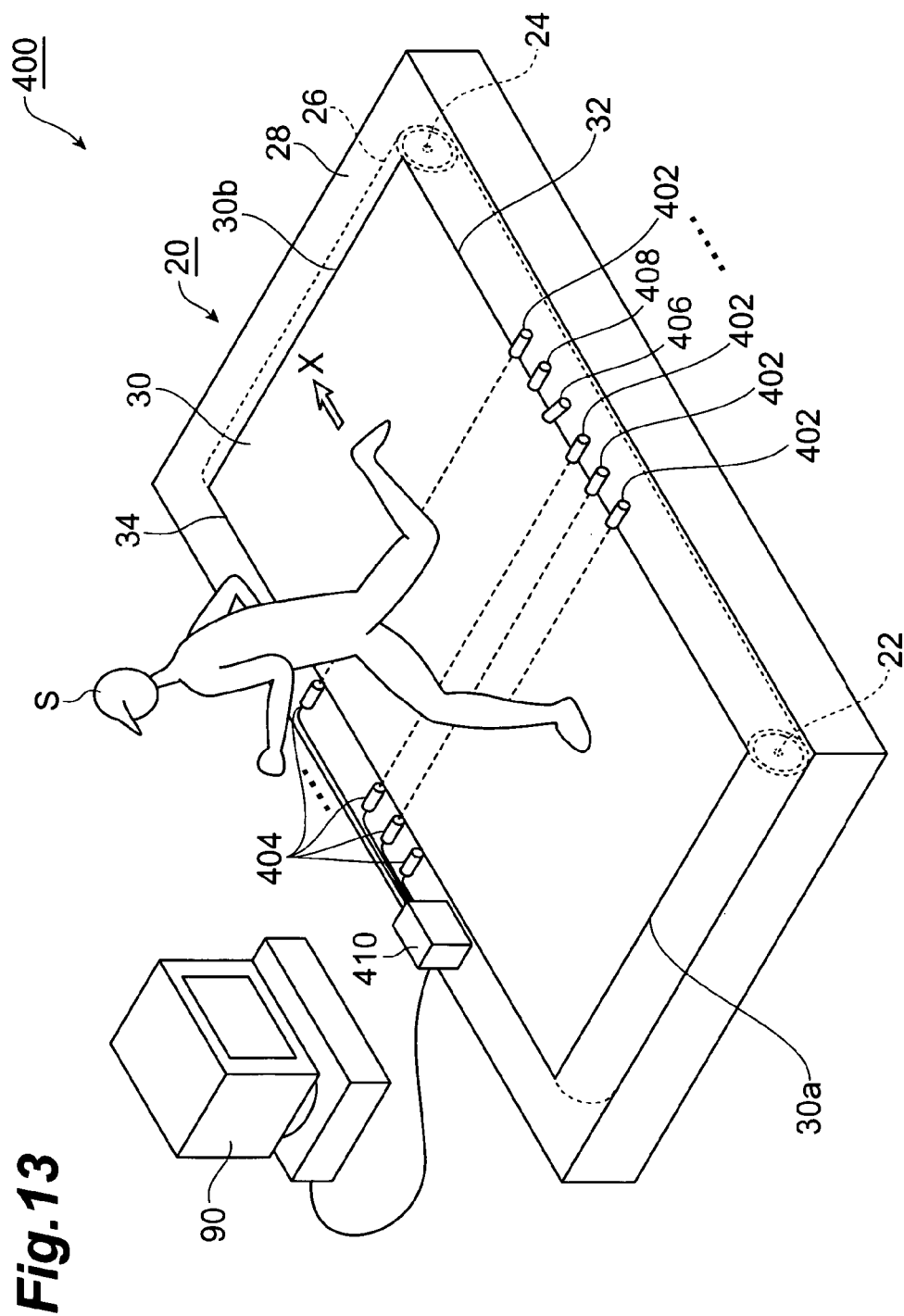
FIG. 13 is a perspective view schematically showing a stride measuring apparatus according to the fifth embodiment of the present invention.

A stride measuring apparatus according to the fifth embodiment of the present invention will be described below. FIG. 13 is a perspective view schematically showing the stride measuring apparatus according to the fifth embodiment of the present invention. The stride measuring apparatus 400 shown in FIG. 13 has a treadmill 20 and a computer 90 similar to those in the stride measuring apparatus 10 of the first embodiment. Furthermore, the stride measuring apparatus 400 has a plurality of signal wave emitters (signal wave emitting means) 402, a plurality of signal wave detectors (signal wave detecting means) 404, a second signal wave emitter (second signal wave emitting means) 406, a second signal wave detector (second signal wave detecting means) 408, and a calculation part 410.

Each of the signal wave emitters 402 is placed at a position along an edge part of running surface 30 and is a predetermined distance apart from an adjacent signal wave detector 402. In the present embodiment, the plurality of signal wave emitters 402 are provided on the cover 28 extending along the edge part 32. Each of the signal wave emitters 402 emits a signal wave in a direction intersecting with the predetermined direction X and at a predetermined height above the running surface 30. This signal wave can be, for example, a light beam. The predetermined height is similar to the height of the light beam L1 relative to the running surface 30 in the first embodiment.

Each of the signal wave detectors 404 is placed at a position along an edge part of the running surface 30 and is configured to receive a signal wave emitted from a corresponding signal wave emitter 402. In the present embodiment, the plurality of signal wave detectors 404 are placed on the cover 28 extending along the edge part 34.

The plurality of signal wave detectors 404 output a first signal when a foot of the subject passes across a signal wave, and output a second signal when no foot of the subject pass across a signal wave. In the present embodiment, when a foot of the subject passes across a signal wave or a light beam from a signal wave emitter 402 to intercept the light beam, a corresponding signal wave detector 404 outputs an OFF signal to the calculation part 410. On the other hand, when no foot of the subject passes across a light beam from a signal wave emitter 402 and when the light beam is received, a corresponding signal wave detector 404 outputs an ON signal to the calculation part 410.

The second signal wave emitter 406 is placed at a position along an edge part of the running surface 30. The second signal wave emitter 406 emits a second signal wave in a direction intersecting with the predetermined direction X. The second signal wave emitter 406 outputs an emission time of the second signal wave to the calculation part 410. In the present embodiment, the second signal wave emitter 406 is placed on the cover 28 extending along the edge part 32 and emits an ultrasonic wave as the second signal wave.

The second signal wave detector 408 receives a reflected wave of the second signal wave at a position along an edge part of the running surface 30. The second signal wave detector 408 outputs a reception time of the second signal wave to the calculation part 410. In the present embodiment, the second signal wave detector 408 is placed on the cover 28 extending along the edge part 32 and the second signal wave detector 408 receives the ultrasonic wave emitted from the second signal wave emitter 406 and reflected by a foot of the subject.

Figure 14:
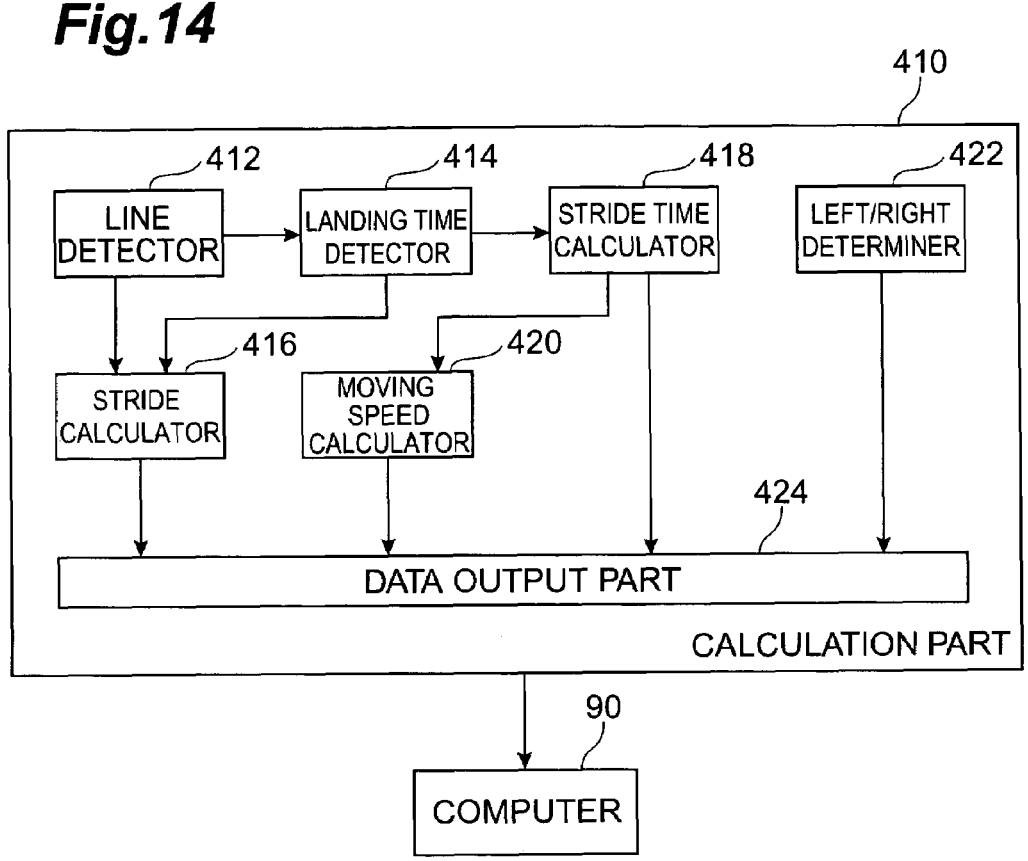
FIG. 14 is an illustration showing a configuration of a calculation part in the fifth embodiment of the present invention.

The calculation part 410 will be described below. FIG. 14 is an illustration showing a configuration of the calculation part according to the fifth embodiment. The calculation part 410 shown in FIG. 14 is physically comprised of a processor, and elements such as a memory. The calculation part 410 is functionally comprised of a line detector (line detecting means) 412, a landing time detector (landing time detecting means) 414, a stride calculator (stride calculating means) 416, a stride time calculator 418, a moving speed calculator (moving speed calculating means) 420, a left/right determiner (left/right determining means) 422, and a data output part 424.

The line detector 412 receives signals (ON signals and OFF signals) from the signal wave detectors 404. Each signal wave detector 404 detects a fall time Ts and a rise time Tr of an OFF signal in a format to enable identification of the signal wave detector 404 as an output source of the signal. For example, the line detector 412 determines through which signal line a signal was transmitted out of a plurality of signal lines connecting the line detector 412 to the plurality of signal wave detectors 404, thereby identifying a signal wave detector 404 being an output source of the signal.

In the description hereinafter, for convenience' sake of description, "i" will denote an identification number of each signal wave detector 404 and identification numbers of integers will be given in increasing order from 1 to the signal wave detectors 404 from one closest to one end of the running surface 30a. A fall time and a rise time represented by $Ts_i$ and $Tr_i$ will denote a fall time Ts and a rise time Tr, respectively, detected based on a signal from a signal wave detector 404 with an identification number i.

Figure 15:
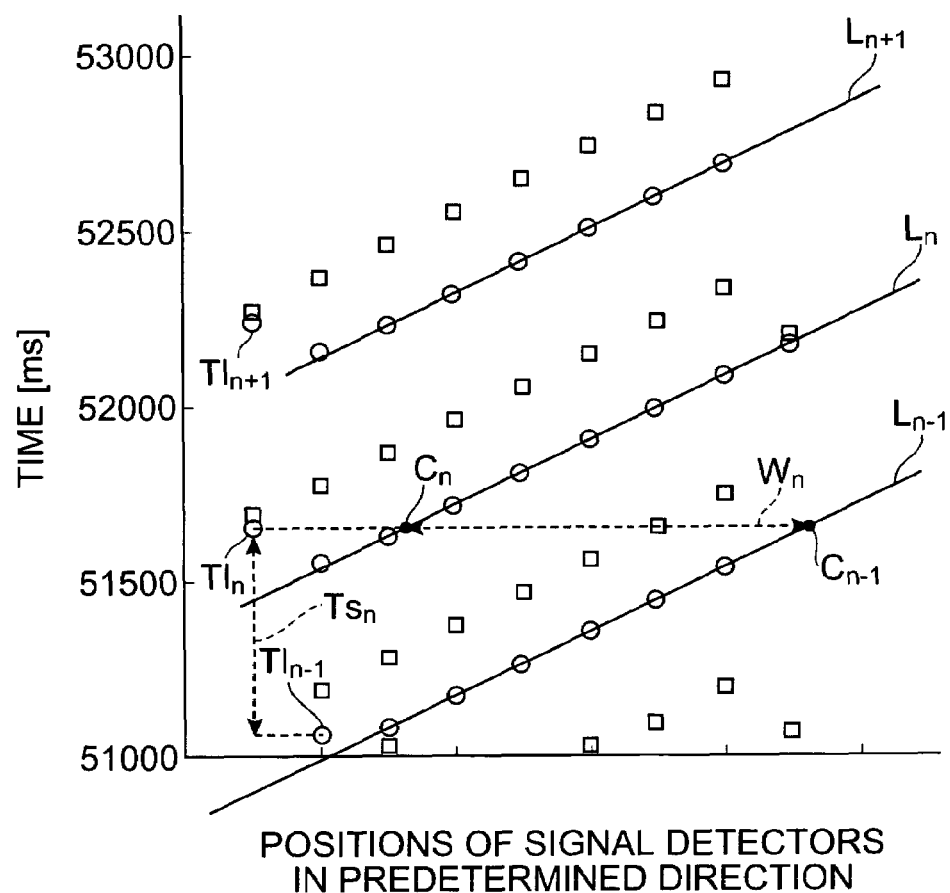
FIG. 15 is an illustration showing a concept of a line detection process by a line detector.

FIG. 15 is an illustration showing the concept of the line detection process by the line detector. In FIG. 15, the horizontal axis represents the positions of the signal wave detectors 404 in the predetermined direction X, and the vertical axis the time. In FIG. 15, outline circles represent variables with the fall time Ts as one parameter, and outline squares variables with the rise time Tr as one parameter.

The line detector 412 generates variables containing parameters of the fall time $Ts_i$ outputted from each signal wave detector 404 or the rise time $Tr_i$ outputted from each signal wave detector 404, and the position of the corresponding signal wave detector 404 in the predetermined direction X. The line detector 412 generates a variable set consisting of a group of variables acquired by passage of a subject's foot in the predetermined direction X on the running surface 30. The line detector 412 detects a line that fits the variable set. A case where the fall time Ts is a parameter in the variables will be described below.

In order to detect a line to fit a variable set, the line detector 412 calculates a slope Sl according to Eq (1) below, using the ith variable and the (i+1)th variable in the order of the positions of the signal wave detectors 404 being the parameter of the variables from the closest to one end 34a.

$$\text{Slope } Sl = \frac{\text{(distance between } i\text{th signal detector and } (i+1)\text{th signal detector)}}{Ts_{i+1} - Ts_i} \quad (1)$$

The line detector 412 starts from i=2 in Eq (1) and, where a predetermined number of slopes are stable, for example, the line detector 412 detects a line having a slope in the case of i=2 according to Eq (1) and passing the variable of i=2. FIG. 15 shows lines $L_{n-1}$, $L_n$, $L_{n+1}$ detected by the line detector 412. Here "n" represents an index to indicate an order in the direction of time.

The landing time detector 414 detects a landing time of a subject's foot on the running surface 30. In order to detect the landing time, the landing time detector 414 detects a variable whose error relative to the line $L_n$ detected using the variable set is within a predetermined value, the variable containing as a parameter the position closest to one end 30a, as the position of the signal detector 404, out of the variables contained in the above variable set. The landing time detector 414 detects from the above variable set a variable containing as parameters a fall time Ts later than the fall time Ts included in the detected variable, and a position closer to one end 30a than the position included in the detected variable. The landing time detector 414 detects the fall time Ts included in the detected variable, as a landing time $Tl_n$ (cf. FIG. 15).

The stride calculator 416 calculates a stride of the subject S. Specifically, the stride calculator 416 detects intersecting points $C_n$, $C_{n-1}$ of a line passing the landing time Tl, with the line $L_n$ and with the line $L_{n-1}$. The stride calculator 416 calculates as a stride $W_n$ a distance in the predetermined direction x specified from the intersecting points $C_n$, $C_{n-1}$ (cf. FIG. 15).

The stride time calculator 418 calculates a time necessary for a step of the subject S, i.e., a stride time. The stride time calculator 418 calculates a period of time between the landing time $Tl_n$ and the landing time $Tl_{n-1}$ and defines the period as the stride time $Ts_n$ (cf. FIG. 15).

The moving speed calculator 420 calculates a foot speed of the subject S (moving speed). The moving speed calculator 420 determines the foot speed $V_n$ of the subject S from the result of the quotient calculation between the stride $S_n$ and the stride time $Ts_n$.

The left/right determiner 422 determines whether the aforementioned stride $W_n$, stride time $Ts_n$, and foot speed $V_n$ are those of the left foot or the right foot of the subject S. Specifically, the left/right determiner 422 receives an emission time of the second signal wave from the second signal wave emitter 406 and receives a reception time of the reflected wave of the second signal wave from the second signal wave detector 408. The left/right determiner 422 calculates a difference between the reception time and the emission time to calculate a propagation time $Tt_n$. The left/right determiner 422 compares the propagation time $Tt_n$ with a propagation time $Tt_{n-1}$ calculated immediately prior thereto, whereby, where the propagation time $Tt_n$ is shorter, it outputs a result of the determination of being the left foot in the present embodiment.

The data output part 424 outputs data containing the aforementioned stride $W_n$, stride time $Ts_n$, foot speed $V_n$, and determination result of the left or right foot, to the computer 90. The computer 90 receives the data from the data output part 424 and outputs a screen about the stride $W_n$, stride time $Ts_n$, foot speed $V_n$, and determination result of the left or right foot included in the data. The computer 90 can output, for example, a screen showing a graph of the stride $W_n$, stride time $Ts_n$, foot speed $V_n$, and determination result of the left or right foot included in the data.

Figure 16:
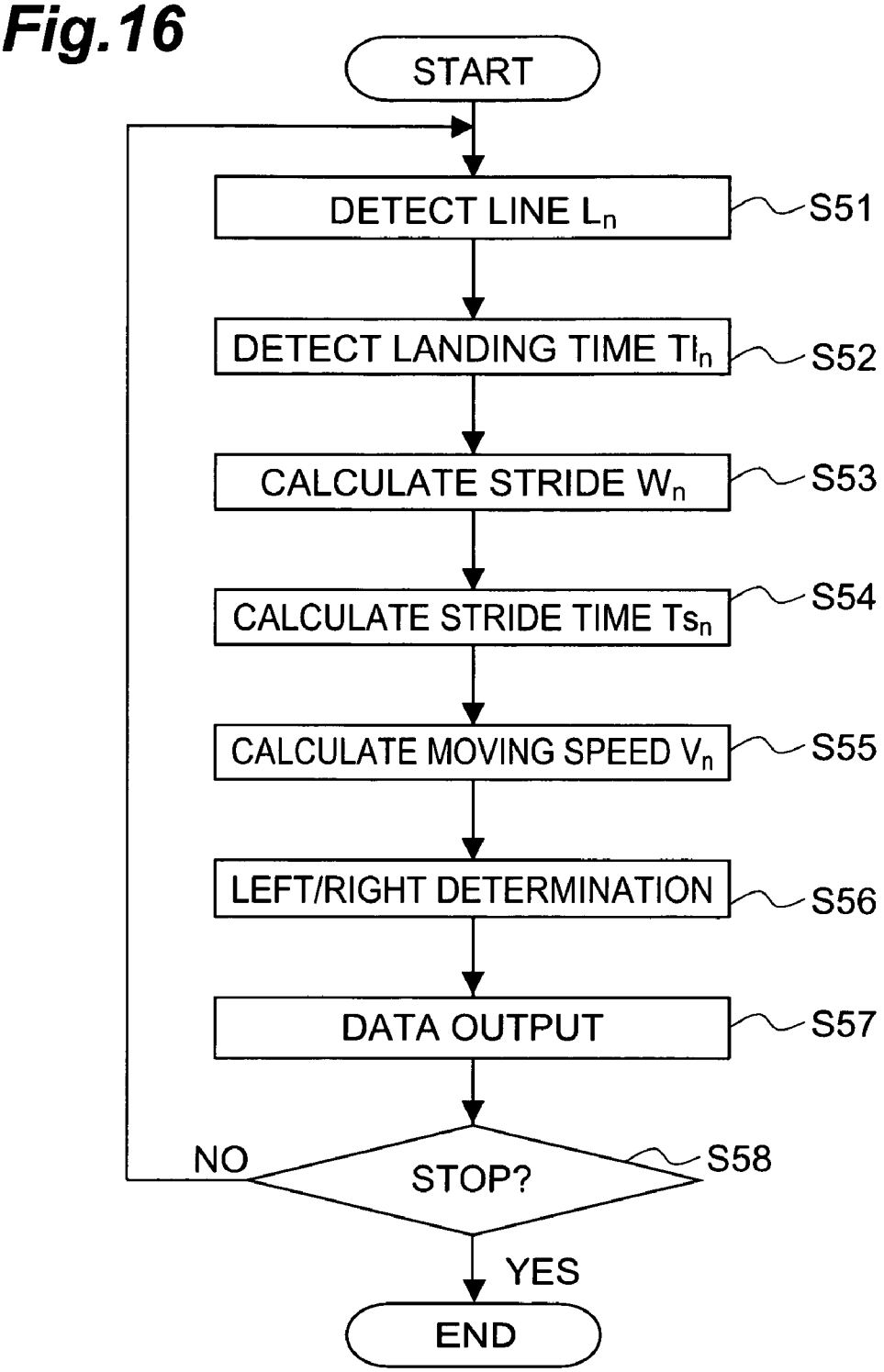
FIG. 16 is a flowchart showing an operation of the calculation part in the fifth embodiment of the present invention.

The operation of the calculation part 410 will be described below. FIG. 16 is a flowchart showing the operation of the calculation part according to the fifth embodiment of the present invention. As shown in FIG. 16, the calculation part 410 first detects the line $L_n$ from the aforementioned variable set (step S51). Then the landing time detector 414 detects the landing time $Tl_n$, using the variable set and the line $L_n$ (step S52).

Next, the stride calculator 416 detects the intersecting points $C_n$, $C_{n-1}$ of a line passing the landing time $Tl_n$ with the line $L_n$ and with the line $L_{n-1}$ and calculates as a stride $W_n$ the distance specified by the intersecting points $C_n$, $C_{n-1}$ (step S53).

Next, the stride time calculator 418 calculates as a stride time $Ts_n$ a period of time between the landing time $Tl_n$ and the landing time $Tl_{n-1}$ (step S54). Then the moving speed calculator 420 performs a calculation of a quotient between the stride $W_n$ and the stride time $Ts_n$ to calculate the foot speed (moving speed) $V_n$ of the subject (step S55).

Subsequently, the left/right determiner 422 determines whether the stride $W_n$, moving speed $V_n$, and stride time $Ts_n$ are those of the left foot or the right foot of the subject S as described above (step S56), and the data output part 424 outputs data containing the stride $W_n$, moving speed $V_n$, stride time $Ts_n$, and the determination result by the left/right determiner 422, to the computer 90 (step S57). Through the above steps, the stride $W_n$, moving speed $V_n$, stride time $Ts_n$, and determination result of the left or right foot are displayed on the screen of the computer 90.

It is then detected whether the operation of the treadmill 20 is stopped by the subject (step S58). When it is stopped, the operation of the calculation part 410 is terminated. When it is not stopped on the other hand, the sequential operation from step S51 is repeated.

As described above about the predetermined embodiments, the present invention successfully provides the compact stride measuring apparatus that can be installed in a narrow space, because the subject's stride can be calculated by means of the signal wave emitting means and signal wave detecting means at positions along an edge part of the running surface, as a sensor.

The principles of the present invention have been illustrated and described in the preferred embodiments, but it is apparent to a person skilled in the art that the present invention can be modified in arrangement and detail without departing from such principles. We, therefore, claim rights to all variations and modifications coming with the spirit and the scope of claims.

What is claimed is:

1. A stride measuring apparatus comprising:
 a belt having a running surface for a subject to run or walk, the belt being driven in a predetermined direction;
 light beam emitting means placed at a position along an edge part of the running surface for emitting a light beam in a direction intersecting with the predetermined direction and so that the light beam maintains a predetermined height above the running surface;
 light beam detecting means placed at an edge part of the running surface and for receiving the light beam emitted by the light beam emitting means and to output a first signal when the light beam detecting means does not receive the light beam emitted from the light beam emitting means, and a second signal when the light beam detecting means detects the light beam emitted from the light beam emitting means;
 moving speed calculating means for calculating a moving time based on a calculation of a difference between a rise time and a fall time of one first signal out of two first signals outputted in succession from the light beam detecting means, and for calculating a moving speed of the subject on the basis of a calculation of a quotient between a size of the foot of the subject and the moving time;
 stride time calculating means for calculating a stride time based on a calculation of a difference between output times of said two first signals;
 stride calculating means for calculating a stride of the subject, based on a calculation of a product between the stride time calculated by the stride time calculating means and the moving speed calculated by the moving speed calculating means;

second light beam emitting means placed at a position along an edge part of the running surface for emitting a second light beam in a direction intersecting with the predetermined direction and so that the second light beam maintains a predetermined height above the running surface and is inclined at a predetermined angle relative to the emission direction of the light beam;

second light beam detecting means placed at a position along an edge part of the running surface for receiving the second light beam emitted by the second light beam emitting means and to output a first signal when the second light beam detecting means does not receive the second light beam emitted from the second light beam emitting means, and a second signal when the second light beam detecting means receives the second light beam emitted by the second light beam emitting means; and left/right determining means for determining whether the stride calculated by the stride calculating means is a stride of the left foot or a stride of the right foot of the subject, based on a comparison of a time difference between first signals respectively outputted from the light beam detecting means and from the second light beam detecting means, with a time difference between first signals respectively outputted in succession from the light beam detecting means and from the second light beam detecting means.

2. The stride measuring apparatus according to claim 1, wherein the light beam emitting means is placed at a position along one edge part of the running surface, and wherein the light beam detecting means is placed at a position along another edge part of the running surface and opposite the light beam emitting means and is configured to output the first signal when the light beam from the light beam emitting means is intercepted, and to output the second signal when the light beam from the light beam emitting means is detected.

3. The stride measuring apparatus according to claim 1, wherein the light beam emitting means is placed at a position along one edge part of the running surface, and wherein the light beam detecting means is placed at a position along said one edge part of the running surface so as to detect the light beam emitted from the light beam emitting means and reflected from a foot of the subject, and is configured to output the first signal when the light beam is detected, and to output the second signal when the light beam is not detected.

4. The stride measuring apparatus according to claim 1, further comprising moving time removing means for removing the moving time calculated by the moving speed calculating means, when the moving time calculated by the moving speed calculating means is determined to be shorter, based on a comparison according to a predetermined rule with a moving time calculated at a different time by the moving speed calculating means.

5. A stride measuring apparatus comprising:

a belt having a running surface for a subject to run or walk, the belt being driven in a predetermined direction;

first light beam emitting means placed at a position along an edge part of the running surface for emitting a first light beam in a direction intersecting with the predetermined direction and so that the first light beam maintains a predetermined height above the running surface;

second light beam emitting means placed a predetermined distance apart from the first light beam emitting means in the predetermined direction and configured to emit a second light beam in a direction intersecting with the predetermined direction and and so that the second light beam maintains a predetermined height above the running surface;

first light beam detecting means placed at an edge part of the running surface and configured to receive the first light beam emitted by the first light beam emitting means and to output a first signal when the first light beam detecting means does not receive the first light beam emitted from the first light beam emitting means, and a second signal when the first light beam detecting means receives the first light beam emitted from the first light beam emitting means;

second light beam detecting means placed at an edge part of the running surface for receiving the second light beam emitted by the second light beam emitting means and to output a first signal when the second light beam detecting means does not receive the first light beam emitted from the second light beam emitting means, and a second signal when the second light beam detecting means receives the second light beam emitted from the first light beam emitting means;

moving speed calculating means for calculating a moving time based on a calculation of a difference between an output time of a first signal outputted from the first light beam detecting means and an output time of a first signal outputted subsequently thereto from the second light beam detecting means, and for calculating a moving speed of the subject on the basis of a calculation of a quotient between the predetermined distance and the moving time;

stride time calculating means for calculating a stride time based on a calculation of a difference between output times of two first signals outputted in succession from one of the first and second light beam detecting means; and stride calculating means for calculating a stride of the subject, based on a calculation of a product between the stride time calculated by the stride time calculating means and the moving speed calculated by the moving speed calculating means.

6. The stride measuring apparatus according to claim 5, further comprising:

third light beam emitting means placed at a position along an edge part of the running surface for emitting a third light beam in a direction intersecting with the predetermined direction and at a predetermined height above the running surface so as to be inclined at a predetermined angle relative to the emission direction of the first and second light beams;

third light beam detecting means placed at an edge part of the running surface and configured to receive the third light beam emitted by the third light beam emitting means and to output a first signal when the third light beam detecting means does not receive the third light beam emitted from the third light beam emitting means, and a second signal when the third light beam detecting means receives the first light beam emitted from the third light beam emitting means; and left/right determining means for determining whether the stride calculated by the stride calculating means is a stride of the left foot or a stride of the right foot of the subject, based on a comparison of a time difference between output times of first signals respectively outputted from one of the first and second light beam detecting means and from the third light beam detecting means, with a time difference between output times of first signals respectively outputted in succession from said one light beam detecting means and from the third light beam detecting means.

7. The stride measuring apparatus according to claim 5, wherein the first and second light beam emitting means are placed at positions along one edge part of the running surface,
   wherein the first light beam detecting means is placed at a position along another edge part of the running surface and opposite the first light beam emitting means, and is configured to output the first signal when the first light beam from the first light beam emitting means is intercepted, and to output the second signal when the light beam from the first light beam emitting means is detected, and
   wherein the second light beam detecting means is placed at a position along the other edge part of the running surface and opposite the second light beam emitting means, and is configured to output the first signal when the second light beam from the second light beam emitting means is intercepted, and to output the second signal when the light beam from the second light beam emitting means is detected.

8. The stride measuring apparatus according to claim 5, wherein the first and second light beam emitting means are placed at positions along one edge part of the running surface,
   wherein the first light beam detecting means is placed at a position along one edge part of the running surface so as to detect the first light beam emitted from the first light beam emitting means and reflected from a foot of the subject, and is configured to output the first signal when the first light beam is detected, and to output the second signal when the first light beam is not detected, and
   wherein the second light beam detecting means is placed at a position along one edge part of the running surface so as to detect the second light beam emitted from the second light beam emitting means and reflected from a foot of the subject, and is configured to output the first signal when the second light beam is detected, and to output the second signal when the second light beam is not detected.

9. The stride measuring apparatus according to claim 5, wherein the moving speed calculating means calculates as the moving speed an average of a first moving speed calculated based on a rise time of a first signal outputted from the first light beam detecting means and a rise time of a first signal outputted subsequently thereto from the second light beam detecting means and a second moving speed calculated based on fall times of the first signals.

10. The stride measuring apparatus according to claim 5, further comprising moving time removing means for removing the moving time calculated by the moving speed calculating means, when the moving time calculated by the moving speed calculating means is determined to be shorter, based on a comparison according to a predetermined rule with a moving time calculated at a different time by the moving speed calculating means.

11. A stride measuring apparatus comprising:
   a belt having a running surface for a subject to run or walk, the belt being driven in a predetermined direction;
   a plurality of light beam emitting means placed at positions along an edge part of the running surface and at predetermined intervals, each for emitting a light beam in a direction intersecting with the predetermined direction and at a predetermined height above the running surface;
   a plurality of light beam detecting means placed at positions along an edge part of the running surface, each for receiving a light beam emitted by a corresponding light beam emitting means, to output a first signal when the light beam detecting means do not receive the light beam emitted from the corresponding light beam emitting means, and to output a second signal when the light beam detecting means receive the light beam emitted from the corresponding light beam emitting means;
   line detecting means for detecting a line that fits a variable set containing variables with parameters of an output time of the first signal or the second signal outputted from the light beam detecting means, and the position of the light beam detecting means, the variable set being obtained with movement of a foot of the subject in the predetermined direction; and
   stride calculating means for calculating a stride, based on a distance between intersecting points of a line passing an arbitrary time, with two lines detected in succession by the line detecting means.

12. The stride measuring apparatus according to claim 11, wherein the running surface of the belt is driven in the predetermined direction from one end to another end,
   the stride measuring apparatus further comprising landing time detecting means for detecting a variable whose error relative to the line detected with use of the variable set is within a predetermined value, said variable containing as a parameter a position closest to said one end, out of the variables in the variable set, for detecting a variable containing as parameters an output time later than an output time included in the detected variable, and a position on the one end side with respect to the position included in the detected variable, and for detecting the output time included in the detected variable, as a landing time.

13. The stride measuring apparatus according to claim 12, further comprising moving speed detecting means for calculating a foot speed, based on a calculation of a quotient between a stride time and the stride, where the stride time is a duration between two landing times detected in succession by the landing time detecting means.

14. The stride measuring apparatus according to claim 11, further comprising:
   second light beam emitting means placed at a position along an edge part of the running surface for emitting a second light beam in a direction intersecting with the predetermined direction;
   second light beam detecting means for receiving a reflected wave of the second light beam; and
   left/right determining means for determining whether the stride calculated by the stride calculating means is a stride of the left foot or a stride of the right foot of the subject, based on a period of time between an emission time and a reception time of the second light beam.

* * * * *